United States Patent
Knight et al.

(10) Patent No.: US 11,710,536 B2
(45) Date of Patent: *Jul. 25, 2023

(54) METHODS AND SYSTEMS FOR IDENTIFYING TARGET GENES

(71) Applicant: Algen Biotechnologies, Inc., San Francisco, CA (US)

(72) Inventors: Spencer Charles Knight, San Francisco, CA (US); Chun-Hao Huang, San Francisco, CA (US)

(73) Assignee: Algen Biotechnologies, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/735,494

(22) Filed: May 3, 2022

(65) Prior Publication Data

US 2022/0262459 A1 Aug. 18, 2022

Related U.S. Application Data

(63) Continuation of application No. 17/556,068, filed on Dec. 20, 2021, which is a continuation of application No. PCT/US2020/038435, filed on Jun. 18, 2020.

(60) Provisional application No. 62/865,033, filed on Jun. 21, 2019.

(51) Int. Cl.
| | |
|---|---|
| *G16B 20/00* | (2019.01) |
| *G16B 40/20* | (2019.01) |
| *C12N 5/09* | (2010.01) |
| *C12N 9/22* | (2006.01) |
| *C12N 15/10* | (2006.01) |
| *C12N 15/11* | (2006.01) |
| *C12N 15/86* | (2006.01) |
| *G06N 20/00* | (2019.01) |

(52) U.S. Cl.
CPC ........... *G16B 20/00* (2019.02); *C12N 5/0693* (2013.01); *C12N 5/0694* (2013.01); *C12N 9/22* (2013.01); *C12N 15/1058* (2013.01); *C12N 15/1089* (2013.01); *C12N 15/1096* (2013.01); *C12N 15/11* (2013.01); *C12N 15/86* (2013.01); *G06N 20/00* (2019.01); *G16B 40/20* (2019.02); *C12N 2310/20* (2017.05); *C12N 2740/15043* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 2018/0257075 A1 | 9/2018 | Yellen et al. | |
| 2022/0254440 A1* | 8/2022 | Knight | C12N 15/11 |

FOREIGN PATENT DOCUMENTS

| | | |
|---|---|---|
| WO | WO-2019018693 A2 | 1/2019 |
| WO | WO-2020257455 A1 | 12/2020 |

OTHER PUBLICATIONS

Huang, C.W. et al., "Neural autoregressive flows", Proceedings of the 35th International Conference on Machine Learning, Stockholm, Sweden, PMLR 80, 2018, pp. 1-16.
King, G.J.W., et al., "A standardized method for assessment of elbow function", Research Committee, American Shoulder and Elbow Surgeons. J Shoulder Elbow Surg., Jul.-Aug. 1999;8(4):351-354.
PCT/US2020/038435 International Preliminary Report on Patentability dated Dec. 21, 2021.
PCT/US2020/038435 International Search Report with Written Opinion dated Oct. 2, 2020.
Tabor, S. et al. A single residue in DNA polymerases of the *Escherichia coli* DNA polymerase I family is critical for distinguishing between deoxy- and dideoxyribonucleotides. Proc. Natl. Acad. Sci. USA, 92:14 (1995) pp. 6339-6343.

* cited by examiner

*Primary Examiner* — Nancy J Leith
(74) *Attorney, Agent, or Firm* — Wilson Sonsini Goodrich & Rosati

(57) ABSTRACT

The present disclosure provides methods and systems for identification of genomic regions for therapeutic targeting. A method for identifying one or more genomic regions for therapeutic targeting, which may facilitate re-programming of a cell from one phenotypic state to another, may comprise: providing single-cell RNA-seq data for a plurality of diseased cells and a plurality of normal cells of a cell type; mapping the single-cell RNA-seq data for the plurality of diseased cells and the plurality of normal cells into a latent space corresponding to a plurality of phenotypic states of the cell type; identifying, based at least in part on a topology of the latent space, the one or more genomic regions for therapeutic targeting; and electronically outputting the one or more genomic regions for therapeutic targeting.

22 Claims, 21 Drawing Sheets

METHODS AND SYSTEMS FOR IDENTIFYING TARGET GENES

CROSS-REFERENCE

This application is a continuation of U.S. patent application Ser. No. 17/556,068, filed Dec. 20, 2021, which is a continuation of International Application No. PCT/US2020/038435, filed Jun. 18, 2020, which claims the benefit of U.S. Provisional Application No. 62/865,033, filed Jun. 21, 2019, each of which is incorporated by reference herein in its entirety.

BACKGROUND

The ability to convert cells from one differentiated state to another may hold great promise for therapeutic applications. However, despite the promise of cellular re-programming, the identification of genetic drivers that may mediate the transition between one cell state to another remains challenging for many therapeutically relevant applications. The phenotype of re-programming may be complex and may involve many genes interacting with each other in a hierarchical, non-linear fashion. Disentangling which of these genes is causal versus correlative in a given process may be a challenging task and may require extensive, time-intensive experimental assays and animal models for each gene of interest.

SUMMARY

Recognized herein is a need for improved methods of identifying genomic regions for therapeutic targeting, which may facilitate re-programming of a cell from one phenotypic state to another. Methods and systems provided herein may significantly increase the efficient, accuracy, and/or throughput of identification of such genomic regions for therapeutic targeting, which may facilitate re-programming of a cell from one phenotypic state to another.

The present disclosure relates generally to methods and systems for quantifying transcriptional re-programming of cells from one differentiated state to another. In particular, the present technology relates to high-content, high-efficiency, and high-throughput CRISPR (clustered regularly interspaced short palindromic repeats) screening techniques for identifying relevant target genes that may potentially mediate re-programming between phenotypically distinct cellular states and/or be selected as effective therapeutic targets. These screens may leverage anomaly detection models to quantify re-programming as a measurable phenotype for each gene that is targeted via CRISPR. Methods and systems of the present disclosure may establish quantification of re-programming as a basis for choosing biomarkers and therapeutic targets relevant to a disease indication of interest.

In an aspect, the present disclosure provides a method for quantifying transcriptional transitions ("re-programming") between differentiated or phenotypically distinct cell populations. The method may comprise: (a) single-cell RNA-seq profiling of the distinct cell populations; (b) supervised dimensionality reduction of single-cell RNA-seq profiles into a topologically representative latent space; (c) identification of potential genetic drivers ("genes") that mediate transitions between the cell populations via systems biology approaches; (d) interrogation of potential genetic drivers via a pooled CRISPR editing experiment; and (e) application of anomaly detection methods to quantify the extent of transcriptional re-programming from one distinct phenotypic state to the other for each genetic driver that is interrogated.

In another aspect, the present disclosure provides a method for identifying biomarkers and potential therapeutic target genes for a variety of disease indications. The method may comprise: (a) identification of appropriate disease and target cell populations; (b) identification of potential genetic drivers mediating the transition between disease and target cell populations as described above; and (c) quantification of re-programming for each of the genetic drivers as described above. In other embodiments, multiple biomarkers or target genes may be identified via combinatorial inhibition or activation of multiple genes.

In some embodiments, the cell populations are derived from relevant tissue(s) of healthy or diseased patients corresponding to the indication of interest. In other embodiments, the cell populations are derived from primary cell lines, human organoids, animal models, or other appropriate model systems. In some cases, the disease cell populations are characterized by a specific genotypic signature, such as a specific mutation(s) in a gene(s) of interest.

In some embodiments, the target cell population corresponds to a fully differentiated state derived from healthy tissue, wild-type primary cell lines, organoids, animal models, or other appropriate model systems. In other embodiments, the target cell population corresponds to an intermediate state, such as: stem cells, precancerous cells, senescent cells, or progenitor cells relevant to disease progression.

In some embodiments, the CRISPR system is selected from the group consisting of: CRISPR (e.g., active Cas9), CRISPRi (e.g., CRISPR interference, a catalytically dead Cas9 fused to a transcriptional repressor peptide including KRAB), CRISPRa (e.g., CRISPR activation, a catalytically dead Cas9 fused to a transcriptional activator peptide including VPR (HIV viral protein R)), RNAi, and shRNA.

Another aspect described herein is a method for identifying one or more genomic regions that facilitate re-programming of a cell from one phenotypic state to another, said method comprising: providing single-cell ribonucleic acid (RNA) sequence data for a plurality of diseased cells and a plurality of normal cells of a cell type; mapping said single-cell RNA sequence data for said plurality of diseased cells and said plurality of normal cells into a latent space corresponding to a plurality of phenotypic states of said cell type; identifying, based at least in part on a topology of said latent space, said one or more genomic regions that facilitate re-programming of said cell type between a first phenotypic state and a second phenotypic state of said plurality of phenotypic states, wherein said one or more genomic regions are configured to be edited to facilitate said re-programming of said cell type between said first phenotypic state and said second phenotypic state; and electronically outputting said one or more genomic regions.

In one embodiment, said mapping comprises using a dimensionality reduction algorithm. In one embodiment, said dimensionality reduction algorithm comprises a uniform manifold approximation and projection (UMAP) algorithm. In one embodiment, said UMAP algorithm is a supervised UMAP algorithm. In one embodiment, said supervised UMAP algorithm has been trained on single-cell RNA sequence data of pure cells of said cell type. In on embodiment, said UMAP algorithm has been trained using a minimum distance of about 0.025-0.25.

In one embodiment, said identifying comprises: conducting non-linear cell trajectory reconstruction on said latent space to construct an inferred maximum likelihood progression trajectory between said first phenotypic state and said second phenotypic state; and based on said inferred maximum likelihood progression trajectory, using probabilistic inference to identify said one or more genomic regions that facilitate re-programming of said cell type between said first phenotypic state and said second phenotypic state.

In one embodiment, conducting said non-linear cell trajectory reconstruction comprises applying the reverse graph embedding algorithm to said latent space. In one embodiment, said first phenotypic state is cancer and said second phenotypic state is a wild-type state.

In one embodiment, the method further comprises: prior to said mapping, removing low-frequency genomic regions from said single-cell RNA sequence data for said plurality of diseased cells and said plurality of normal cells. In one embodiment, the method further comprises: for a respective genomic region of said one or more genomic regions, using a genomic editing unit to edit said respective genomic region to facilitate said re-programming of a cell of said cell type between said first phenotypic state and said second phenotypic state. In one embodiment, said genomic editing unit is selected from the group consisting of a CRISPR system, a CRISPRi system, CRISPRa system, an RNAi system, and an shRNA system.

In one embodiment, the method further comprises: measuring, using an anomaly detection algorithm, a quantity of a shift in said latent space of said cell as a result of using said genomic editing unit to edit said respective genomic region.

In one embodiment, said anomaly detection algorithm has been trained on latent space profiles of a plurality of cell types. In one embodiment, said plurality of cell types comprises pancreatic ductal cells, pancreatic acinar cells, pancreatic adenocarcinomas, and/or pancreatic adenocarcinomas. In one embodiment, said anomaly detection algorithm comprises one or more of: a density-based technique, a subspace-based outlier detection, a correlation-based outlier detection, a tensor-based outlier detection, a support vector machine (SVM), a single-class vector machine, support vector data description, a neural network, a Bayesian network, a hidden Markov model (HMM), a cluster analysis-based outlier detection, deviation from association rules and frequent itemsets, fuzzy logic-based outlier detection, and an ensemble technique. In one embodiment, said anomaly detection algorithm is a support vector machine (SVM), a density-based technique, a k-nearest neighbor algorithm, a local outlier factor algorithm, or an isolation forest algorithm. In one embodiment, said anomaly detection algorithm is a support vector machine. In one embodiment, said anomaly detection algorithm is an isolation forest algorithm.

In one embodiment, the method further comprises: measuring a distance (e.g., a Chebychev distance, a Correlation distance, a Cosine distance, a Euclidean distance, a signed Euclidean distance, a Hamming distance, a Jaccard distance, a Kullback-Leibler distance, a Mahalanobis distance, a Manhattan distance, a Minkowski distance, or a Spearman distance) of a shift in said latent space of said cell as a result of using said genomic editing unit to edit said respective genomic region. In one embodiment, the method further comprises: using said genomic editing unit to edit each of said one or more genomic regions to facilitate said re-programming of a respective cell of said cell type between said first phenotypic state and said second phenotypic state; measuring a quantity of a shift in said latent space of each of said cells as a result of using said genomic editing unit to edit said respective genomic region; and using said measured quantities, ranking said one or more genes for therapeutic targeting.

In one embodiment, the method further comprises: measuring, using a density estimation function (e.g., a probability density estimation, a rescaled histogram, a parametric density estimation function, a non-parametric density estimation function (e.g., a kernel density function), or a data clustering technique (e.g., vector quantization)), a quantity of a shift in said latent space of said cell as a result of using said genomic editing unit to edit said respective genomic region. In one embodiment, said cell type is a pancreatic cell. In one embodiment, said diseased cells are cancer cells. In one embodiment, said plurality of diseased cells and said plurality of normal cells are selected from the group consisting of primary cell lines, human organoids, and animal models.

In one embodiment, the method further comprises generating said single-cell RNA sequence data for a plurality of diseased cells and a plurality of normal cells of a cell type. In one embodiment, said second phenotypic state is an intermediate state. In one embodiment, said intermediate state is a precancerous state or a less malignant state.

In one embodiment, the method further comprises: based on said one or more genomic regions, identifying one or more therapeutic targets to treat a disease associated with said first phenotypic state.

In one embodiment, the method further comprises: identifying, based at least in part on a topology of said latent space, one or more first genomic regions that facilitate re-programming of said cell type between said first phenotypic state and an intermediate phenotypic state of said plurality of phenotypic states, wherein said one or more first genomic regions are configured to be edited to facilitate re-programming of said cell type between said first phenotypic state and said intermediate phenotypic state; and identifying, based at least in part on a topology of said latent space, one or more second genomic regions that facilitate re-programming of said cell type between said intermediate phenotypic state and said second phenotypic state of said plurality of phenotypic states, wherein said one or more second genomic regions are configured to be edited to facilitate re-programming of said cell type between said intermediate phenotypic state and said second phenotypic state.

Another aspect described herein is a method for identifying one or more genomic regions that facilitate re-programming of a cell from one phenotypic state to another, said method comprising: providing single-cell ribonucleic acid (RNA) sequence data for a plurality of diseased cells and a plurality of normal cells of a cell type; mapping, using a supervised dimensionality reduction algorithm, said single-cell RNA sequence data for said plurality of diseased cells and said plurality of normal cells into a latent space corresponding to a plurality of phenotypic states of said cell type; identifying, based at least on a topology of said latent space, said one or more genomic regions that facilitate re-programming of said cell type between a first phenotypic state and a second phenotypic state of said plurality of phenotypic states, wherein said one or more genomic regions are configured to be edited to facilitate said re-programming of said cell type between said first phenotypic state and said second phenotypic state; electronically outputting said one or more genomic regions; for a respective genomic region of said one or more genomic regions, using a genomic editing unit to edit said respective genomic region to facilitate said re-programming of a cell of said cell type between said first phenotypic state and said second phenotypic state; and measuring, using an anomaly detection algorithm, a quantity of a shift in said latent space of said cell as a result of using said genomic editing unit to edit said respective genomic region. In one embodiment, said supervised dimensionality reduction algorithm is a variable auto-encoder.

Another aspect described herein is a system for identifying one or more genomic regions that facilitate re-programming of a cell from one phenotypic state to another, comprising: a database that comprises single-cell ribonucleic acid (RNA) sequence data for a plurality of diseased cells and a plurality of normal cells of a cell type; and one or more computer processors that are individually or collectively programmed to: map said single-cell RNA sequence data for said plurality of diseased cells and said plurality of normal cells into a latent space corresponding to a plurality of phenotypic states of said cell type; identify, based at least in part on a topology of said latent space, said one or more genomic regions that facilitate re-programming of said cell type between a first phenotypic state and a second phenotypic state of said plurality of phenotypic states, wherein said one or more genomic regions are configured to be edited to facilitate said re-programming of said cell type between said first phenotypic state and said second phenotypic state; and electronically output said one or more genomic regions.

In one embodiment, said mapping comprises using a dimensionality reduction algorithm. In one embodiment, said dimensionality reduction algorithm comprises a uniform manifold approximation and projection (UMAP) algorithm.

Another aspect described herein is a non-transitory computer-readable medium comprising machine-executable code that, upon execution by one or more computer processors, implements a method for identifying one or more genomic regions that facilitate re-programming of a cell from one phenotypic state to another, said method comprising: providing single-cell ribonucleic acid (RNA) sequence data for a plurality of diseased cells and a plurality of normal cells of a cell type; mapping said single-cell RNA sequence data for said plurality of diseased cells and said plurality of normal cells into a latent space corresponding to a plurality of phenotypic states of said cell type; identifying, based at least in part on a topology of said latent space, said one or more genomic regions that facilitate re-programming of said cell type between a first phenotypic state and a second phenotypic state of said plurality of phenotypic states, wherein said one or more genomic regions are configured to be edited to facilitate said re-programming of said cell type between said first phenotypic state and said second phenotypic state; and electronically outputting said one or more genomic regions.

In one embodiment, said mapping comprises using a dimensionality reduction algorithm. In one embodiment, said dimensionality reduction algorithm comprises a uniform manifold approximation and projection (UMAP) algorithm.

Another aspect described herein is a system for identifying one or more genomic regions that facilitate re-programming of a cell from one phenotypic state to another, comprising: a database that comprises single-cell ribonucleic acid (RNA) sequence data for a plurality of diseased cells and a plurality of normal cells of a cell type; and one or more computer processors that are individually or collectively programmed to: map, using a supervised dimensionality reduction algorithm, said single-cell RNA sequence data for said plurality of diseased cells and said plurality of normal cells into a latent space corresponding to a plurality of phenotypic states of said cell type; identify, based at least on a topology of said latent space, said one or more genomic regions that facilitate re-programming of said cell type between a first phenotypic state and a second phenotypic state of said plurality of phenotypic states, wherein said one or more genomic regions are configured to be edited to facilitate said re-programming of said cell type between said first phenotypic state and said second phenotypic state; electronically output said one or more genomic regions; for a respective genomic region of said one or more genomic regions, use a genomic editing unit to edit said respective genomic region to facilitate said re-programming of a cell of said cell type between said first phenotypic state and said second phenotypic state; and measure, using an anomaly detection algorithm, a quantity of a shift in said latent space of said cell as a result of using said genomic editing unit to edit said respective genomic region.

Another aspect described herein is a non-transitory computer-readable medium comprising machine-executable code that, upon execution by one or more computer processors, implements a method for identifying one or more genomic regions that facilitate re-programming of a cell from one phenotypic state to another, said method comprising: providing single-cell ribonucleic acid (RNA) sequence data for a plurality of diseased cells and a plurality of normal cells of a cell type; mapping, using a supervised dimensionality reduction algorithm, said single-cell RNA sequence data for said plurality of diseased cells and said plurality of normal cells into a latent space corresponding to a plurality of phenotypic states of said cell type; identifying, based at least on a topology of said latent space, said one or more genomic regions that facilitate re-programming of said cell type between a first phenotypic state and a second phenotypic state of said plurality of phenotypic states, wherein said one or more genomic regions are configured to be edited to facilitate said re-programming of said cell type between said first phenotypic state and said second phenotypic state; electronically outputting said one or more genomic regions; for a respective genomic region of said one or more genomic regions, using a genomic editing unit to edit said respective genomic region to facilitate said re-programming of a cell of said cell type between said first phenotypic state and said second phenotypic state; and measuring, using an anomaly detection algorithm, a quantity of a shift in said latent space of said cell as a result of using said genomic editing unit to edit said respective genomic region.

Another aspect described herein is a method for identifying one or more genomic regions for therapeutic targeting, said method comprising: providing single-cell ribonucleic acid (RNA) sequence data for a plurality of diseased cells and a plurality of normal cells of a cell type; mapping said single-cell RNA sequence data for said plurality of diseased cells and said plurality of normal cells into a latent space; identifying, based at least in part on a topology of said latent space, said one or more genomic regions for therapeutic targeting; and electronically outputting said one or more genomic regions for identifying therapeutic targets.

In one embodiment, said mapping comprises using a dimensionality reduction algorithm. In one embodiment, said dimensionality reduction algorithm comprises a uniform manifold approximation and projection (UMAP) algorithm.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
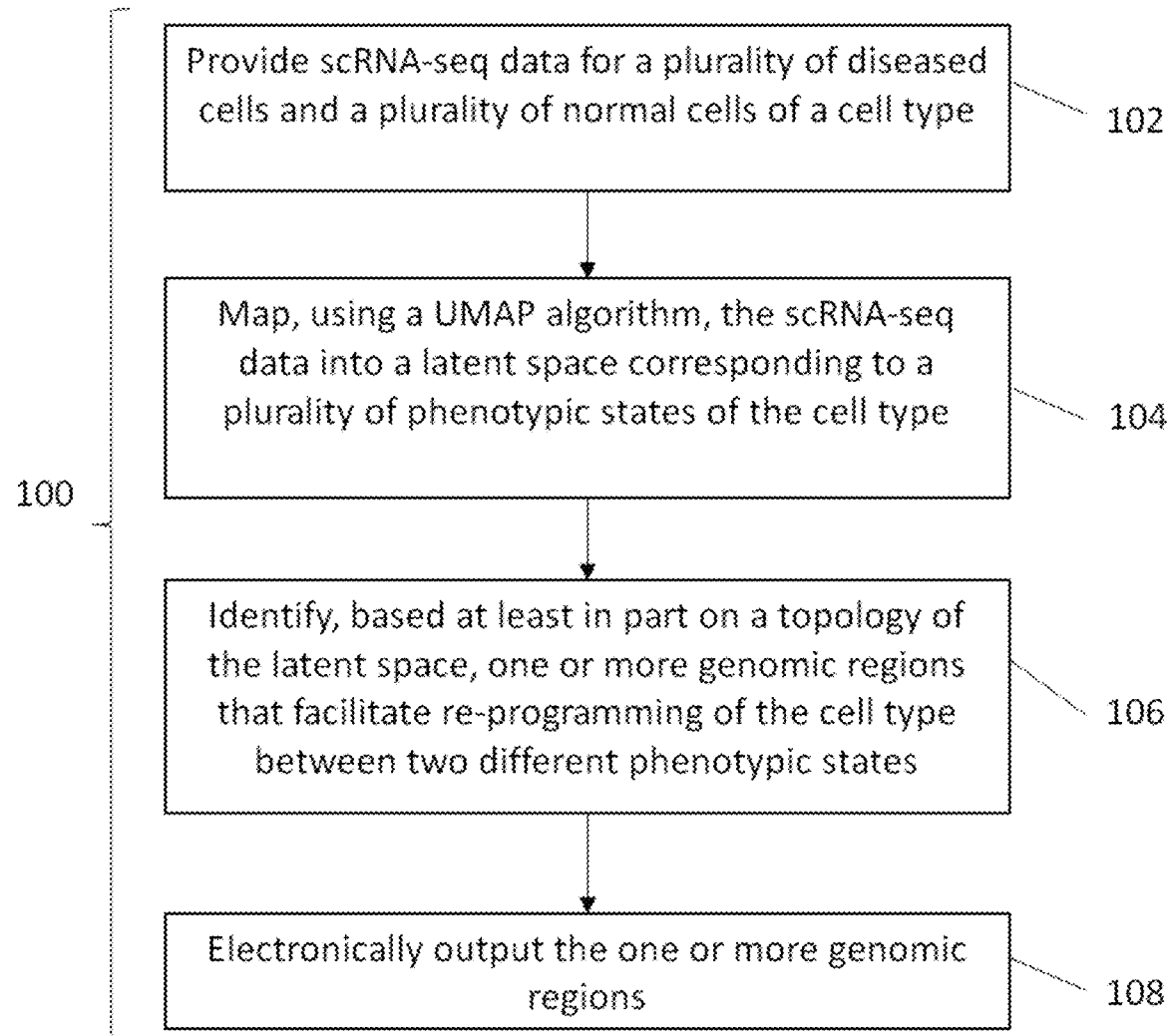
FIG. 1 shows an example of a flowchart illustrating methods of identification of re-programming target genes, in accordance with disclosed embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "sequencing," as used herein, generally refers to a process for generating or identifying a sequence of a biological molecule, such as a nucleic acid molecule. Such sequence may be a nucleic acid sequence, which may include a sequence of nucleic acid bases. Sequencing methods may be massively parallel array sequencing (e.g., Illumina sequencing), which may be performed using template nucleic acid molecules immobilized on a support, such as a flow cell or beads. Sequencing methods may include, but are not limited to: high-throughput sequencing, next-generation sequencing, sequencing-by-synthesis, flow sequencing, massively-parallel sequencing, shotgun sequencing, single-molecule sequencing, nanopore sequencing, pyrosequencing, semiconductor sequencing, sequencing-by-ligation, sequencing-by-hybridization, RNA-Seq (Illumina), Digital Gene Expression (Helicos), Single Molecule Sequencing by Synthesis (SMSS) (Helicos), Clonal Single Molecule Array (Solexa), and Maxim-Gilbert sequencing.

The term "subject," as used herein, generally refers to an individual having a biological sample that is undergoing processing or analysis. A subject may be an animal or plant. The subject may be a mammal, such as a human, ape, monkey, chimpanzee, dog, cat, horse, pig, rodent (e.g., mouse or rat), reptile, amphibian, or bird. The subject may have or be suspected of having a disease, such as cancer (e.g., breast cancer, colorectal cancer, brain cancer, leukemia, lung cancer, skin cancer, liver cancer, pancreatic cancer, lymphoma, esophageal cancer, or cervical cancer) or an infectious disease.

The term "sample," as used herein, generally refers to a biological sample. Examples of biological samples include tissues, cells, nucleic acid molecules, amino acids, polypeptides, proteins, carbohydrates, fats, metabolites, hormones, and viruses. In an example, a biological sample is a nucleic acid sample including one or more nucleic acid molecules, such as deoxyribonucleic acid (DNA) and/or ribonucleic acid (RNA). The nucleic acid molecules may be cell-free or cell-free nucleic acid molecules, such as cell-free DNA or cell-free RNA. The nucleic acid molecules may be derived from a variety of sources including human, mammal, non-human mammal, ape, monkey, chimpanzee, reptilian, amphibian, or avian, sources. Further, samples may be extracted from variety of animal fluids containing cell-free sequences, including but not limited to blood, serum, plasma, vitreous, sputum, urine, tears, perspiration, saliva, semen, mucosal excretions, mucus, spinal fluid, amniotic fluid, lymph fluid and the like. Cell-free polynucleotides may be fetal in origin (via fluid taken from a pregnant subject), or may be derived from tissue of the subject itself.

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate (PO$_3$) groups. A nucleotide may include a nucleobase, a five-carbon sugar (either ribose or deoxyribose), and one or more phosphate groups.

Ribonucleotides are nucleotides in which the sugar is ribose. Deoxyribonucleotides are nucleotides in which the sugar is deoxyribose. A nucleotide may be a nucleoside monophosphate or a nucleoside polyphosphate. A nucleotide may be a deoxyribonucleoside polyphosphate, such as, e.g., a deoxyribonucleoside triphosphate (dNTP), which may be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide may include any subunit that may be incorporated into a growing nucleic acid strand. Such subunit may be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double-stranded. In some cases, a nucleic acid molecule is circular.

The terms "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or ribonucleotides (RNA), or analogs thereof. A nucleic acid molecule may have a length of at least about 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation may be input into databases in a computer having a central processing unit and used for bioinformatics applications such as functional genomics and homology searching. Oligonucleotides may include one or more nonstandard nucleotide(s), nucleotide analog(s), and/or modified nucleotides.

The term "nucleotide analogs," as used herein, may include, but are not limited to, diaminopurine, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, phosphoroselenoate nucleic acids, and the like. In some cases, nucleotides may include modifications in their phosphate moieties, including modifications to a triphosphate moiety. Additional, non-limiting examples of modifications include phosphate chains of greater length (e.g., a phosphate chain having 4, 5, 6, 7, 8, 9, 10, or more than 10 phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure may provide higher density in bits per cubic millimeter (mm), higher safety (e.g., resistance to accidental or purposeful synthesis of natural toxins), easier discrimination in photo-programmed polymerases, or lower secondary structure. Nucleotide analogs may be capable of reacting or bonding with detectable moieties for nucleotide detection.

The term "free nucleotide analog" as used herein, generally refers to a nucleotide analog that is not coupled to an additional nucleotide or nucleotide analog. Free nucleotide analogs may be incorporated in to the growing nucleic acid chain by primer extension reactions.

The term "primer(s)," as used herein, generally refers to a polynucleotide which is complementary to the template nucleic acid. The complementarity or homology or sequence identity between the primer and the template nucleic acid may be limited. The length of the primer may be between 8 nucleotide bases to 50 nucleotide bases. The length of the primer may be greater than or equal to 6 nucleotide bases, 7 nucleotide bases, 8 nucleotide bases, 9 nucleotide bases, 10 nucleotide bases, 11 nucleotide bases, 12 nucleotide bases, 13 nucleotide bases, 14 nucleotide bases, 15 nucleotide bases, 16 nucleotide bases, 17 nucleotide bases, 18 nucleotide bases, 19 nucleotide bases, 20 nucleotide bases, 21 nucleotide bases, 22 nucleotide bases, 23 nucleotide bases, 24 nucleotide bases, 25 nucleotide bases, 26 nucleotide bases, 27 nucleotide bases, 28 nucleotide bases, 29 nucleotide bases, 30 nucleotide bases, 31 nucleotide bases, 32 nucleotide bases, 33 nucleotide bases, 34 nucleotide bases, 35 nucleotide bases, 37 nucleotide bases, 40 nucleotide bases, 42 nucleotide bases, 45 nucleotide bases, 47 nucleotide bases, or 50 nucleotide bases.

A primer may exhibit sequence identity or homology or complementarity to the template nucleic acid. The homology or sequence identity or complementarity between the primer and a template nucleic acid may be based on the length of the primer. For example, if the primer length is about 20 nucleic acids, it may contain 10 or more contiguous nucleic acid bases complementary to the template nucleic acid.

The term "primer extension reaction," as used herein, generally refers to the binding of a primer to a strand of the template nucleic acid, followed by elongation of the primer(s). It may also include, denaturing of a double-stranded nucleic acid and the binding of a primer strand to either one or both of the denatured template nucleic acid strands, followed by elongation of the primer(s). Primer extension reactions may be used to incorporate nucleotides or nucleotide analogs to a primer in template-directed fashion by using enzymes (polymerizing enzymes).

The term "polymerase," as used herein, generally refers to any enzyme capable of catalyzing a polymerization reaction. Examples of polymerases include, without limitation, a nucleic acid polymerase. The polymerase may be naturally occurring or synthesized. In some cases, a polymerase has relatively high processivity. An example polymerase is a Φ29 polymerase or a derivative thereof. A polymerase may be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT® DNA polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some cases, the polymerase is a single subunit polymerase. The polymerase may have high processivity, namely the capability of the polymerase to consecutively incorporate nucleotides into a nucleic acid template without releasing the nucleic acid template. In some cases, a polymerase is a polymerase modified to accept dideoxynucleotide triphosphates, such as for example, Taq polymerase having a 667Y mutation (see e.g., Tabor et al, PNAS, 1995, 92, 6339-6343, which is herein incorporated by reference in its entirety for all purposes). In some cases, a polymerase is a polymerase having a modified nucleotide binding, which may be useful for nucleic acid sequencing, with non-limiting examples that include Thermo Sequenas™ thermostable DNA polymerase (GE Life Sciences), AmpliTaq® FS (ThermoFisher) DNA polymerase, and Sequencing Pol polymerase (Jena Bioscience). In some cases, the polymerase is genetically engineered to have discrimination against dideoxynucleotides, such, as for example, Sequenase™ thermostable DNA polymerase (ThermoFisher).

The term "support," as used herein, generally refers to a solid support such as a slide, a bead, a resin, a chip, an array, a matrix, a membrane, a nanopore, or a gel. The solid support may, for example, be a bead on a flat substrate (such as glass, plastic, silicon, etc.) or a bead within a well of a substrate. The substrate may have surface properties, such as textures, patterns, microstructure coatings, surfactants, or any combination thereof to retain the bead at a desire location (such as in a position to be in operative communication with a detector). The detector of bead-based supports may be configured to maintain substantially the same read rate independent of the size of the bead. The support may be a flow cell or an open substrate. Furthermore, the support may comprise a biological support, a non-biological support, an organic support, an inorganic support, or any combination thereof. The support may be in optical communication with the detector, may be physically in contact with the detector, may be separated from the detector by a distance, or any combination thereof. The support may have a plurality of independently addressable locations. The nucleic acid molecules may be immobilized to the support at a given independently addressable location of the plurality of independently addressable locations. Immobilization of each of the plurality of nucleic acid molecules to the support may be aided by the use of an adaptor. The support may be optically coupled to the detector. Immobilization on the support may be aided by an adaptor.

The term "label," as used herein, generally refers to a moiety that is capable of coupling with a species, such as, for example, a nucleotide analog. In some cases, a label may be a detectable label that emits a signal (or reduces an already emitted signal) that can be detected. In some cases, such a signal may be indicative of incorporation of one or more nucleotides or nucleotide analogs. In some cases, a label may be coupled to a nucleotide or nucleotide analog, which nucleotide or nucleotide analog may be used in a primer extension reaction. In some cases, the label may be coupled to a nucleotide analog after the primer extension reaction. The label, in some cases, may be reactive specifically with a nucleotide or nucleotide analog. Coupling may be covalent or non-covalent (e.g., via ionic interactions, Van der Waals forces, etc.). In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl)phosphine (TCEP)) or enzymatically cleavable (e.g., via an esterase, lipase, peptidase, or protease).

In some cases, the label may be optically active. In some embodiments, an optically-active label is an optically-active dye (e.g., fluorescent dye). Non-limiting examples of dyes include SYBR® green dye, SYBR® blue dye, 4',6-Diamidino-2-phenylindole dihydrochloride (DAPI), propidium iodine, Hoeste, SYBR® gold dye, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX™ Blue dye, SYTOX™ Green dye, SYTOX™ Orange dye, POPO™-1 dye, POPO™-3 dye, YOYO™-1 dye, YOYO™-3 dye, TOTO™-1 dye, TOTO™-3 dye, JOJO™-1 dye, LOLO™-1 dye, BOBO™-1 dye, BOBO™-3 dye, PO-PRO™-1 dye, PO-PRO™-3 dye, BO—PRO™-1 dye, BO-PROT™-3 dye, TO-PRO™-1 dye, TO-PRO™-3 dye, TO-PRO™-5 dye, JO-PRO™-1 dye, LO-PRO™-1 dye, YO—PRO™-1 dye, YO—PRO™-3 dye, PicoGreen™ dye, OliGreen™ dye, RiboGreen™ dye, SYBR® Green I dye, SYBR® Green II dye, SYBR® DX dye, SYTO™-40, -41, -42, -43, -44, -45 (blue) dyes, SYTO™-13, -16, -24, -21, -23, -12, -11, -20, -22, -15, -14, -25 (green) dyes, SYTO™-81, -80, -82, -83, -84, -85 (orange) dyes, SYTO™-64, -17, -59, -61, -62, -60, -63 (red) dyes, fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), CellTracker™ Green dye, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor® 350, 405, 430, 488, 532, 546, 555, 568, 594, 610, 633, 635, 647, 660, 680, 700, 750, and 790 dyes, DyLight® 350, 405, 488, 550, 594, 633, 650, 680, 755, and 800 dyes, or other fluorophores.

In some examples, labels may be nucleic acid intercalator dyes. Examples include, but are not limited to ethidium bromide, YOYO™-1 dye, SYBR® Green dye, and EvaGreen® dye. The near-field interactions between energy donors and energy acceptors, between intercalators and energy donors, or between intercalators and energy acceptors may result in the generation of unique signals or a change in the signal amplitude. For example, such interactions may result in quenching (i.e., energy transfer from donor to acceptor that results in non-radiative energy decay) or Forster resonance energy transfer (FRET) (i.e., energy transfer from the donor to an acceptor that results in radiative energy decay). Other examples of labels include electrochemical labels, electrostatic labels, colorimetric labels and mass tags.

The term "quencher," as used herein, generally refers to molecules that can reduce an emitted signal. Labels may be quencher molecules. For example, a template nucleic acid molecule may be designed to emit a detectable signal. Incorporation of a nucleotide or nucleotide analog comprising a quencher may reduce or eliminate the signal, which reduction or elimination is then detected. In some cases, as described elsewhere herein, labeling with a quencher may occur after nucleotide or nucleotide analog incorporation. Examples of quenchers include Black Hole Quencher™ Dyes (Biosearch Technologies) such as BHQ1-0, BHQ-1, BHQ-3, BHQ-10; QSY™ Dye fluorescent quenchers (from Molecular Probes/Invitrogen) such QSY™ 7 dye, QSY™ 9 dye, QSY™ 21 dye, QSY™ 35 dye, and other quenchers such as 4-(dimethylaminoazo)benzene-4-carboxylic acid (Dabcyl) and 4-(Dimethylamino)azobenzene-4'-sulfonyl chloride (Dabsyl); Cy5Q and Cy7Q and Dark Cyanine dyes (GE Healthcare). Examples of donor molecules whose signals may be reduced or eliminated in conjunction with the above quenchers include fluorophores such as Cy3B, Cy3, or Cy5; Dy-Quenchers (Dyomics), such as DYQ-660 and DYQ-661; fluorescein-5-maleimide; 7-diethylamino-3-(4'-maleimidylphenyl)-4-methylcoumarin (CPM); N-(7-dimethylamino-4-methylcoumarin-3-yl) maleimide (DACM) and ATTO fluorescent quenchers (ATTO-TEC GmbH), such as ATTO 540Q, 580Q, 612Q, 647N, Atto-633-iodoacetamide, tetramethylrhodamine iodoacetamide or Atto-488 iodoacetamide. In some cases, the label may be a type that does not self-quench for example, Bimane derivatives such as Monobromobimane.

The term "detector," as used herein, generally refers to a device that is capable of detecting a signal, including a signal indicative of the presence or absence of an incorporated nucleotide or nucleotide analog. In some cases, a detector may include optical and/or electronic components that may detect signals. The term "detector" may be used in detection methods. Non-limiting examples of detection methods include optical detection, spectroscopic detection, electrostatic detection, electrochemical detection, and the like. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The terms "sequence" or "sequence read," as used herein, generally refer to a series of nucleotide assignments (e.g, by base calling) made during a sequencing process. Such sequences may be estimated sequence reads made by making preliminary base calls, which may then be subject to further base calling analysis or correction to produce final sequence reads. Sequences may comprise information corresponding to single or individual cells, and may be obtained by single-cell sequencing techniques (e.g., single-cell RNA sequencing, or scRNA-seq). Single-cell sequencing may be performed to provide a higher resolution of cellular differences and information about the function of an individual cell in the context of its microenvironment. For example, single-cell DNA sequencing can provide information about mutations present in rare cell populations (e.g., found in cancer cells), and single-cell RNA sequencing can provide information about individual cell expression corresponding to the existence and behavior of different cell types.

The terms "single guide RNA" or "sgRNA," as used herein, generally refer to a single RNA molecule that contains both a custom-designed short CRISPR RNA (crRNA) sequence fused to a scaffold trans-activating crRNA (tracrRNA) sequence. The sgRNA can be synthetically generated or made in vitro or in vivo from a DNA template.

The ability to convert cells from one differentiated state to another may hold great promise for therapeutic applications. However, despite the promise of cellular re-programming, the identification of genetic drivers that may mediate the transition between one cell state to another remains challenging for many therapeutically relevant applications. The phenotype of re-programming may be complex and may involve many genes interacting with each other in a hierarchical, non-linear fashion. Disentangling which of these genes is causal versus correlative in a given process may be a challenging task and may require extensive, time-intensive experimental assays and animal models for each gene of interest.

Recognized herein is a need for improved methods of identifying genomic regions for therapeutic targeting, which may facilitate re-programming of a cell from one phenotypic state to another. Methods and systems provided herein may significantly increase the efficient, accuracy, and/or throughput of identification of such genomic regions for therapeutic targeting, which may facilitate re-programming of a cell from one phenotypic state to another.

The present disclosure relates generally to methods and systems for quantifying transcriptional re-programming of cells from one differentiated state to another. In particular, the present technology relates to high-content, high-efficiency, and high-throughput CRISPR (clustered regularly interspaced short palindromic repeats) screening techniques for identifying relevant target genes that may potentially mediate re-programming between phenotypically distinct cellular states and/or be selected as effective therapeutic targets. These screens may leverage anomaly detection models to quantify re-programming as a measurable phenotype for each gene that is targeted via CRISPR. Methods and systems of the present disclosure may establish quantification of re-programming as a basis for choosing biomarkers and therapeutic targets relevant to a disease indication of interest.

In an aspect, the present disclosure provides a method for quantifying transcriptional transitions ("re-programming") between differentiated or phenotypically distinct cell populations. The method may comprise: (a) single-cell RNA-seq profiling of the distinct cell populations; (b) supervised dimensionality reduction of single-cell RNA-seq profiles into a topologically representative latent space; (c) identification of potential genetic drivers ("genes") that mediate transitions between the cell populations via systems biology approaches; (d) interrogation of potential genetic drivers via a pooled CRISPR editing experiment; and (e) application of anomaly detection methods to quantify the extent of transcriptional re-programming from one distinct phenotypic state to the other for each genetic driver that is interrogated.

In another aspect, the present disclosure provides a method for identifying biomarkers and potential therapeutic target genes for a variety of disease indications. The method may comprise: (a) identification of appropriate disease and target cell populations; (b) identification of potential genetic drivers mediating the transition between disease and target cell populations as described above; and (c) quantification of re-programming for each of the genetic drivers as described above. In other embodiments, multiple biomarkers or target genes may be identified via combinatorial inhibition or activation of multiple genes.

In some embodiments, the cell populations are derived from relevant tissue(s) of healthy or diseased patients corresponding to the indication of interest. In other embodiments, the cell populations are derived from primary cell lines, human organoids, animal models, or other appropriate model systems. In some cases, the disease cell populations are characterized by a specific genotypic signature, such as a specific mutation(s) in a gene(s) of interest.

In some embodiments, the target cell population corresponds to a fully differentiated state derived from healthy tissue, wild-type primary cell lines, organoids, animal models, or other appropriate model systems. In other embodiments, the target cell population corresponds to an intermediate state, such as: stem cells, precancerous cells, senescent cells, or progenitor cells relevant to disease progression.

In some embodiments, the CRISPR system is selected from the group consisting of: CRISPR (e.g., active Cas9), CRISPRi (e.g., CRISPR interference, a catalytically dead Cas9 fused to a transcriptional repressor peptide including KRAB), CRISPRa (e.g., CRISPR activation, a catalytically dead Cas9 fused to a transcriptional activator peptide including VPR (HIV viral protein R)), RNAi, and shRNA.

FIG. 1 shows an example of a flowchart illustrating a method 100 of identification of therapeutic targets, such as re-programming target genes, in accordance with disclosed embodiments. The method may comprise providing single-cell ribonucleic acid (RNA) sequence data for a plurality of diseased cells and a plurality of normal cells of a cell type (as in operation 102). In some embodiments, the method may comprise generating the scRNA-seq data for a plurality of diseased cells and a plurality of normal cells. Next, the method may comprise mapping (e.g., using a dimensionality reduction algorithm such as a uniform manifold approximation and projection (UMAP) algorithm) the single-cell RNA sequence data for the plurality of diseased cells and the plurality of normal cells into a latent space corresponding to a plurality of phenotypic states of the cell type (as in operation 104). Alternatively, the mapping may be performed using a supervised dimensionality reduction algorithm, such as a variable auto-encoder. Next, the method may comprise identifying, based at least in part on a topology of the latent space, one or more genomic regions that facilitate re-programming of the cell type between a first phenotypic state and a second phenotypic state of the plurality of phenotypic states (e.g., wherein the one or more genomic regions are configured to be edited to facilitate the re-programming of the cell type between the first phenotypic state and the second phenotypic state) (as in operation 106). For example, the first phenotypic state may be a diseased state (e.g., cancer), and the second phenotypic state may be a non-diseased state (e.g., wild-type or a progenitor state), an earlier disease state (e.g., a precancerous state, an earlier-stage cancer state, or a precursor disease state), or an intermediate disease state (e.g., a less severe or malignant disease state). As another example, the method may further comprises identifying, based at least in part on a topology of a latent space, first genomic regions that facilitate re-programming of the cell type between the first phenotypic state and an intermediate phenotypic state, where the first genomic regions are configured to be edited to facilitate re-programming of the cell type between the first phenotypic state and the intermediate phenotypic state; and identifying, based at least in part on a topology of the latent space, second genomic regions that facilitate re-programming of the cell type between the intermediate phenotypic state and the second phenotypic state, where the second genomic regions are configured to be edited to facilitate re-programming of the cell type between the intermediate phenotypic state and the second phenotypic state. Next, the method may comprise electronically outputting the one or more genomic regions (as in operation 108). In some embodiments, the method may comprise identifying at least one of the genomic regions as therapeutic targets, and/or performing therapeutic targeting of at least one of the genomic regions to treat a subject in need thereof (e.g., having a disease state for which the therapeutic targeting is an effective treatment). For example, the therapeutic targeting may be performed using a small-molecule inhibitor, an antibody therapy, an RNAi, an antisense oligonucleotide, or a combination thereof.

In some embodiments, the UMAP algorithm is a supervised UMAP algorithm or an unsupervised supervised UMAP algorithm. For example, a supervised UMAP algorithm may be trained on a dataset comprising single-cell RNA sequence (scRNA-seq) data of pure cells of a given cell type. The UMAP algorithm may be trained using a minimum distance of about 0.025, about 0.05, about 0.075, about 0.1, about 0.125, about 0.15, about 0.175, about 0.2, about 0.225, about 0.25, about 0.275, about 0.3, about 0.325, about 0.35, about 0.375, about 0.4, about 0.425, about 0.45, about 0.475, about 0.5, about 0.525, about 0.55, about 0.575, about 0.6, about 0.625, about 0.65, about 0.675, about 0.7, about 0.725, about 0.75, about 0.775, about 0.8, about 0.825, about 0.85, about 0.875, about 0.9, about 0.925, about 0.95, about 0.975, or about 1.0. In some embodiments, prior to the mapping, low-frequency genomic regions may be removed from the single-cell RNA sequence (scRNA-seq) data for the plurality of diseased cells and the plurality of normal cells.

The identification of the one or more genomic regions that facilitate re-programming of the cell type between the first phenotypic state and the second phenotypic state may be performed based at any of a number of suitable analyses of a topology of the latent space. As an example, non-linear cell trajectory reconstruction may be conducted on the latent space (e.g., by applying the reverse graph embedding algorithm to the latent space) to construct an inferred maximum likelihood progression trajectory between the first phenotypic state and the second phenotypic state. Then, based on the inferred maximum likelihood progression trajectory, probabilistic inference may be used to identify the one or more genomic regions that facilitate re-programming of the cell type between the first phenotypic state and the second phenotypic state. In some embodiments, one or more therapeutic targets may be identified to treat a disease associated with the first phenotypic state, based on the identified genomic regions.

After the genomic regions are identified, a genomic editing unit (e.g., a CRISPR system, a CRISPRi system, CRISPRa system, an RNAi system, or an shRNA system) may be used to edit a respective genomic region to facilitate the re-programming of a cell of the cell type between the first phenotypic state and the second phenotypic state. After the editing, an anomaly detection algorithm may be used to measure a quantity of a shift in the latent space of the cell as a result of using the genomic editing unit to edit the respective genomic region (e.g., using a density estimation function). For example, the quantity of the shift in the latent space may be measured using a distance measure (e.g., a Chebychev distance, a Correlation distance, a Cosine distance, a Euclidean distance, a signed Euclidean distance, a Hamming distance, a Jaccard distance, a Kullback-Leibler distance, a Mahalanobis distance, a Manhattan distance, a Minkowski distance, a Spearman distance, or a distance on a Riemannian manifold). For example, the density estimation function may comprise a probability density estimation, a rescaled histogram, a parametric density estimation function, a non-parametric density estimation function (e.g., a kernel density function), or a data clustering technique (e.g., vector quantization). The anomaly detection algorithm may comprise an unsupervised machine learning algorithm, a semi-supervised machine learning algorithm, or a supervised machine learning algorithm, which may be trained on latent space profiles of a plurality of cell types, such as diseased cell types (e.g., cancer cells such as pancreatic cancer cells) or non-diseased cell types (e.g., pancreatic cells such as pancreatic ductal or acinar cells). For example, the anomaly detection algorithm may comprise one or more of:

a density-based technique (k-nearest neighbor, local outlier factor, isolation forest), a subspace-based outlier detection, a correlation-based outlier detection, a tensor-based outlier detection, a support vector machine (SVM), a single-class vector machine, support vector data description, a neural network (e.g., replicator neural network, autoencoder, long short-term memory (LSTM) neural network), a Bayesian network, a hidden Markov model (HMM), a cluster analysis-based outlier detection, deviation from association rules and frequent itemsets, fuzzy logic-based outlier detection, and an ensemble technique (e.g., using feature bagging, score normalization, and different sources of diversity). The diseased cells or normal cells may comprise, for example, primary cell lines, human organoids, and animal models. For example, the plurality of cell types may include pancreatic ductal cells, pancreatic acinar cells, pancreatic adenocarcinomas, and/or pancreatic adenocarcinomas. After measuring the quantities of shifts in the latent space of the cell as a result of using the genomic editing unit to edit the respective genomic region, the one or more genes may be ranked for therapeutic targeting based on the measured quantities.

In another aspect, the present disclosure provides a system for identifying one or more genomic regions that facilitate re-programming of a cell from one phenotypic state to another. The system may comprise a database that comprises single-cell RNA sequence data (e.g., for a plurality of diseased cells and a plurality of normal cells of a cell type). The database may be stored locally (e.g., on a local server, computer, or computer media) or remotely (e.g., a cloud-based server). The system may further comprise one or more computer processors that are individually or collectively programmed to implement methods of the present disclosure. For example, the computer processors may be individually or collectively programmed to perform one or more of: mapping (e.g., using a UMAP algorithm or a supervised dimensionality reduction algorithm) the single-cell RNA sequence (scRNA-seq) data for the plurality of diseased cells and the plurality of normal cells into a latent space corresponding to a plurality of phenotypic states of the cell type; identifying, based at least in part on a topology of the latent space, the one or more genomic regions that facilitate re-programming of the cell type between a first phenotypic state and a second phenotypic state of the plurality of phenotypic states (e.g., wherein the one or more genomic regions are configured to be edited to facilitate the re-programming of the cell type between the first phenotypic state and the second phenotypic state); and/or electronically outputting the one or more genomic regions.

Computer Systems

Figure 2:
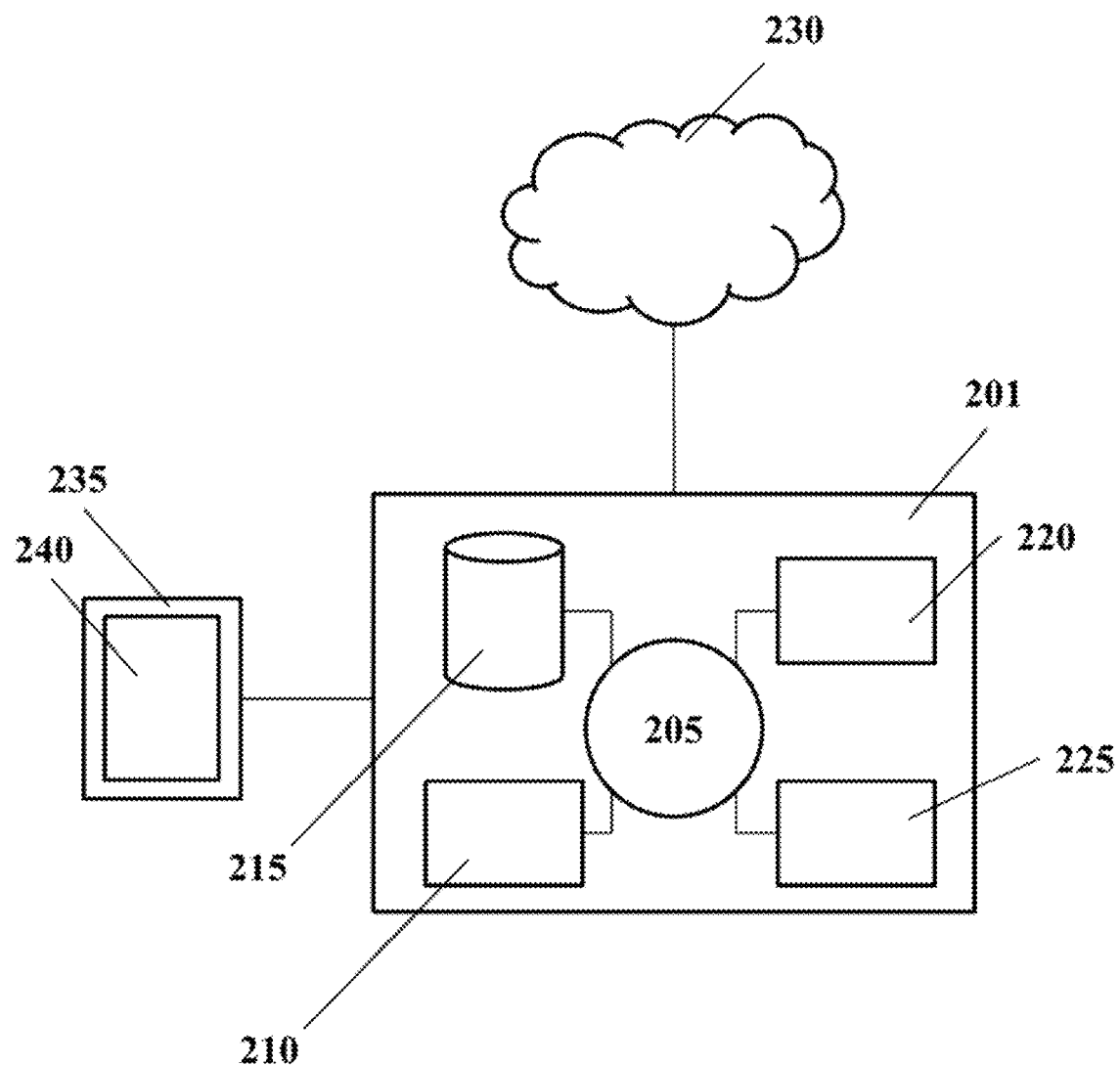
FIG. 2 shows a computer system that is programmed or otherwise configured to implement methods provided herein.

The present disclosure provides computer systems that are programmed to implement methods of the disclosure. FIG. 2 shows a computer system 201 that is programmed or otherwise configured to, for example: generate or analyze scRNA-seq data, map scRNA-seq data into a latent space corresponding to a plurality of phenotypic states (e.g., using a dimensionality reduction algorithm such as UMAP), identify genomic regions that facilitate re-programming of a cell type between a first phenotypic state and a second phenotypic state (e.g., using probabilistic inference), train a supervised algorithm (e.g., supervised UMAP) on scRNA-seq data, conduct non-linear cell trajectory reconstruction on the latent space, remove low-frequency genomic regions from the scRNA-seq data, use a genomic editing unit to edit a genomic region to facilitate re-programming of a cell between a first phenotypic state and a second phenotypic state, use an anomaly detection algorithm to measure a quantity of a shift in the latent space of the cell as a result of using the genomic editing unit to edit the genomic region, train the anomaly detection algorithm on latent space profiles of a plurality of cell types, measure a distance of a shift in the latent space of the cell as a result of using the genomic editing unit to edit the genomic region, rank genes for therapeutic targeting based on the measured quantities of shifts in the latent space of the cell, use a density estimation function to measure the quantity of the shift in the latent space of the cell as a result of using the genomic editing unit to edit the genomic region, and identify therapeutic targets to treat a disease associated with a phenotypic state.

The computer system 201 can regulate various aspects of methods and systems of the present disclosure, such as, for example, generating or analyzing scRNA-seq data, mapping scRNA-seq data into a latent space corresponding to a plurality of phenotypic states (e.g., using a dimensionality reduction algorithm such as UMAP), identifying genomic regions that facilitate re-programming of a cell type between a first phenotypic state and a second phenotypic state (e.g., using probabilistic inference), training a supervised algorithm (e.g., supervised UMAP) on scRNA-seq data, conducting non-linear cell trajectory reconstruction on the latent space, removing low-frequency genomic regions from the scRNA-seq data, using a genomic editing unit to edit a genomic region to facilitate re-programming of a cell between a first phenotypic state and a second phenotypic state, using an anomaly detection algorithm to measure a quantity of a shift in the latent space of the cell as a result of using the genomic editing unit to edit the genomic region, training the anomaly detection algorithm on latent space profiles of a plurality of cell types, measuring a distance of a shift in the latent space of the cell as a result of using the genomic editing unit to edit the genomic region, ranking genes for therapeutic targeting based on the measured quantities of shifts in the latent space of the cell, using a density estimation function to measure the quantity of the shift in the latent space of the cell as a result of using the genomic editing unit to edit the genomic region, and identifying therapeutic targets to treat a disease associated with a phenotypic state.

The computer system 201 can be an electronic device of a user or a computer system that is remotely located with respect to the electronic device. The electronic device can be a mobile electronic device. The computer system 201 includes a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. The network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some cases, the circuit is an application specific integrated circuit (ASIC).

The storage unit 215 can store files, such as drivers, libraries and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine executable or machine readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 201 can include or be in communication with an electronic display 235 that comprises a user interface (UI) 240 for providing, for example, user selection of scRNA-seq data, mapping or other algorithms, and databases. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 205. The algorithm can, for example, generate or analyze scRNA-seq data, map scRNA-seq data into a latent space corresponding to a plurality of phenotypic states (e.g., using a dimensionality reduction algorithm such as UMAP), identify genomic regions that facilitate re-programming of a cell type between a first phenotypic state and a second phenotypic state (e.g., using probabilistic inference), train a supervised algorithm (e.g., supervised UMAP) on scRNA-seq data, conduct non-linear cell trajectory reconstruction on the latent space, remove low-frequency genomic regions from the scRNA-seq data, use a genomic editing unit to edit a genomic region to facilitate re-programming of a cell between a first phenotypic state and a second phenotypic state, use an anomaly detection algorithm to measure a quantity of a shift in the latent space of the cell as a result of using the genomic editing unit to edit the genomic region, train the anomaly detection algorithm on latent space profiles of a plurality of cell types, measure a distance of a shift in the latent space of the cell as a result of using the genomic editing unit to edit the genomic region, rank genes for therapeutic targeting based on the measured quantities of shifts in the latent space of the cell, use a density estimation function to measure the quantity of the shift in the latent space of the cell as a result of using the genomic editing unit to edit the genomic region, and identify therapeutic targets to treat a disease associated with a phenotypic state.

EXAMPLES

Example 1—Generation and Pre-Processing of scRNA-Seq Data

Single-cell RNA sequencing (scRNA-seq) data are generated as follows. Multiple types of pancreatic normal and tumor cells are isolated from mice and cultured, including high-grade cancer cells ($Kras^{G12D}$;$p53^{-/-}$;Myc), low-grade cancer cells ($Kras^{G12D}$;$p53^{-/-}$), and immortalized normal beta, ductal, and acinar cells. These cell lines are further genetically modified to stably express a catalytically dead Cas9 (dCas9) fused to a transcriptional repressor peptide KRAB, enabling CRISPR interference (CRISPRi) for silencing genes of interest. For scRNA-seq, each type of cells is single-cell isolated, and then their corresponding RNA and cDNA libraries are prepared according to the manufacturer's instructions (10× Genomics). The cDNA libraries are sequenced by Miseq (Illumina) to acquire cell number information, and then sequenced by NextSeq or Hiseq4000 (Illumina) to acquire scRNA-seq data.

Pre-processing of scRNA-seq count data is performed as follows. The raw, HGNC-aligned, UMI count matrix generated via 10× sequencing is pre-processed and scaled prior to analyzing in downstream analysis pipelines. Low-abundance genes (e.g., average count <0.1), genes with reads in <10% of cells, and cells with non-zero reads for <10% of all genes are removed from the count matrix (e.g., using SingleCellExperiment, scran, and scater libraries in R). To adjust for discrepancies in sequencing depth between individual cells, count matrices are in some cases normalized and scaled prior to carrying forward in subsequent analyses. Examples of methods of normalization include: globally scaling cell-level counts to the median depth across all cells (scalar adjustment), and solving linear systems to obtain unique scaling factors for individual cells (e.g., using ComputeSumFactors from the scran library in R). In some cases, inter-sample batch effects are corrected via a mutual nearest neighbors algorithm (MNN, e.g., using the mnnCorrect function from the scran library in R).

Example 2—Latent Space Construction

Latent space construction is performed as follows. The high-dimensional, single-cell count matrix is mapped to a 20-100-dimensional latent space using supervised machine learning algorithms. In the case of pancreatic cancer, the reduction algorithm is trained on a collection of pure cell types including pancreatic acinar, ductal, and adenocarcinoma cells. Cells targeted with an essential gene (e.g., PCNA or RPA3) are also included during latent space training in order to model potential toxicity complications that could arise from a target candidate of interest. The labels for supervised learning are chosen to correspond to each of the pure cell types.

Several algorithms are considered for latent space construction, including but not limited to: uniform manifold approximation and projection (UMAP) as well as variable autoencoders (VAEs). In some cases, the Elbow method (e.g., as described by Richards et al., *J Shoulder Elbow Surg* 8(4): 351-354 (1999), which is incorporated herein by reference in its entirety) was used to determine the optimal number of dimensions for the latent space. For UMAP, the following parameters were used for model training: minimum distance of 0.025-0.25, number of neighbors equal to 75% of the total number of cells, and Euclidean distance as the distance metric.

Non-linear cell trajectory reconstruction was conducted via an initial pseudotime ordering of cell populations defining transition states between healthy and diseased endpoints utilizing the Monocle3 package (R) on a reduced dimensionality projection of labeled population data using UMAP manifold learning (Python). A reduced dimensional principal tree defining an inferred maximum likelihood progression trajectory was constructed through the resulting ordering via the Reverse Graph Embedding Algorithm implemented in the DDRTree and Genie3 packages.

Probabilistic inference of driver genes was then conducted via causal gene regulatory network inference utilizing Moran's Test for Spatial Autocorrelation via the Genie3, and Scribe packages (R), exploratory metrics for interactions of mutually influential driver candidates in the inferred trajectory were computed via the Louvain community detection algorithm, and statistical tests reinforcing the robustness of the causality inference were conducted via R implementations of Kendall Tau Correlation and the Granger Causality Test.

The target genes interrogated via a pooled CRISPRi library were quantified in terms of their ability to reprogram cancer cells back to a wild-type-like expression state. Genes were scored via one of several algorithms, including, but not limited to: anomaly detection, density estimation, and pairwise Euclidean distance relative to a pure cell population in the latent space.

Anomaly detection was performed as follows. Separate single-class anomaly detectors were trained on the latent expression profiles of distinct cell types including, but not limited to: pancreatic ductal cells, pancreatic acinar cells, pancreatic adenocarcinomas, and pancreatic adenocarcinomas with an essential gene (e.g., PCNA or RPA3) targeted (via CRISPR/RNAi) as a model for toxicity in healthy tissue. Several algorithms were utilized for anomaly detection including but not limited to: support vector machine (SVM); isolation forests; and support vector data description (SVDD). Each of the trained anomaly detector models was then used to score candidate genes based on the output of the decision function (e.g., a distance to the separating manifold, such as a Chebychev distance, a Correlation distance, a Cosine distance, a Euclidean distance, a signed Euclidean distance, a Hamming distance, a Jaccard distance, a Kullback-Leibler distance, a Mahalanobis distance, a Manhattan distance, a Minkowski distance, or a Spearman distance) applied to the latent expression profiles of single cells targeted with the CRISPRi library.

Density estimation was performed as follows. Separate density estimators were trained on the latent expression profiles of distinct cell types including, but not limited to: pancreatic ductal cells, pancreatic acinar cells, pancreatic adenocarcinomas, and pancreatic adenocarcinomas with an essential gene (e.g., PCNA or RPA3) targeted (via CRISPR/RNAi) as a model for toxicity in healthy tissue. Several algorithms were used to estimate the density functions for each of the cell types including but not limited to: Ball and KD tree estimators; and neural-network-based approaches (e.g., neural autoregressive flow, as described by Huang et al., "Neural autoregressive flows," arXiv:1804.00779, which is incorporate herein by reference in its entirety). For tree-based estimators, one of several kernels was used for training the density function including but not limited to: 1) Gaussian, 2) top-hat, 3) uniform, and 4) Epanechnikov. The trained density estimators for each of the pure cell types were then used to score the latent expression profiles of single cells targeted with the CRISPRi library.

A 5-fold cross-validation was performed for model training and evaluation. For re-programming quantification, cell populations for each of the target genes were repeatedly sampled (25-100×) with replacement in order to construct a bootstrap confidence interval for each target gene.

The outputs of the anomaly detector decision functions (e.g., a distance to the separating manifold, such as a Chebychev distance, a Correlation distance, a Cosine distance, a Euclidean distance, a signed Euclidean distance, a Hamming distance, a Jaccard distance, a Kullback-Leibler distance, a Mahalanobis distance, a Manhattan distance, a Minkowski distance, or a Spearman distance) or density estimators were summarized in several ways in order to determine the optimal target candidate including, but not limited to: mean decision function across all cells silenced for a specific target gene of interest; effect size of the decision function for a specific target gene relative to a non-targeting guide RNA or other control population of interest; and Bonferroni-corrected p-value from a Kolmogorov-Smimov test of the decision function for a specific target gene relative to a non-targeting guide RNA or other control population of interest. In some cases, summary metrics were z-transformed across all target genes. The summarized metrics for each of the anomaly detectors (e.g., primary cells and cancer with negative guides) were further aggregated (e.g., average, Stouffer's method, or Fisher's method). The top-scoring targets that additionally satisfy a p-value threshold for the Kolmogorov-Smimov test on the decision function relative to a negative control population are considered the top re-programming genes and are carried forward for further biological validation.

Figure 3A:
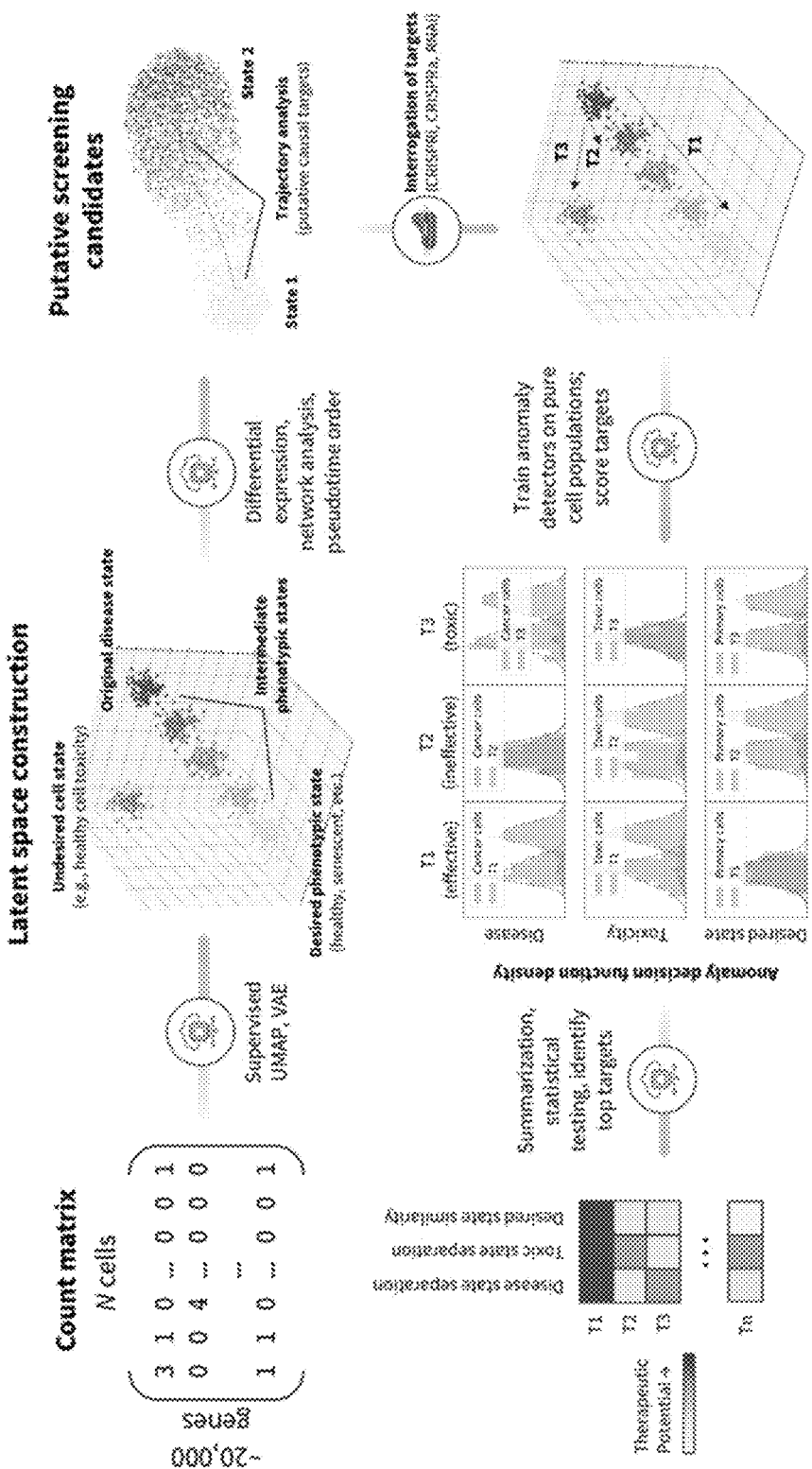
FIG. 3A shows an example of quantification of re-programming and identification of novel therapeutic target genes, in accordance with disclosed embodiments. By leveraging CRISPR (clustered regularly interspaced short palindromic repeats) gene interrogation, intelligent latent space construction, and anomaly detection, target genes are quantified in accordance with their ability to program a diseased cell population towards a desired target phenotypic state. The target state may be derived from a healthy tissue or primary cell line or, alternatively, represent an intermediate state including but not limited to: senescent cells, stem cells, precancerous cells, or progenitor cells relevant to disease progression.
Figure 3B:
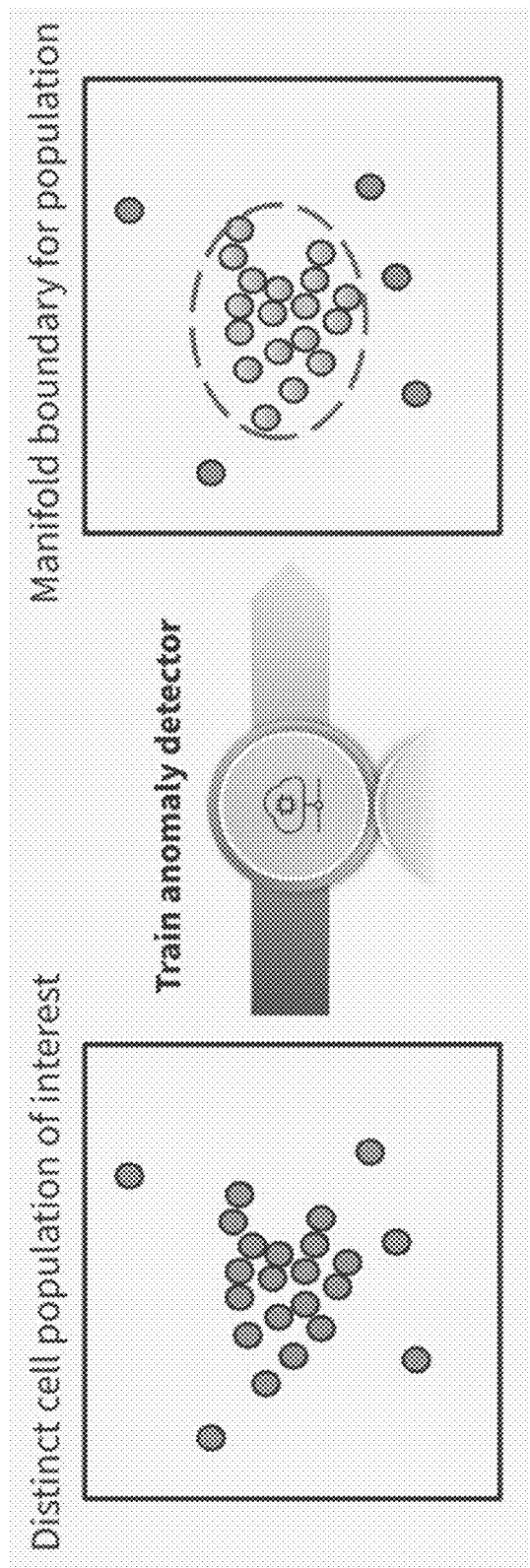
FIG. 3B shows an example of anomaly detection as a method for defining a dense manifold boundary that accurately represents the topological space occupied by a distinct cell population, in accordance with disclosed embodiments.
Figure 3C:
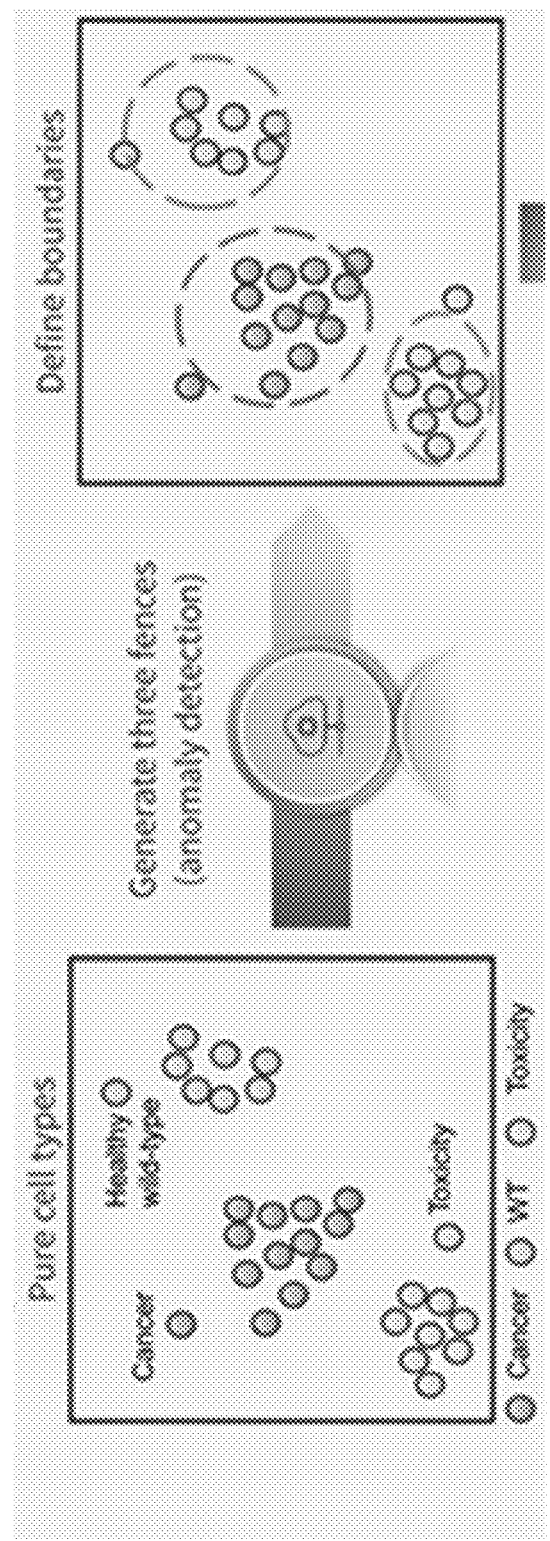
FIG. 3C shows an example of leveraging anomaly detection to identify the top metabolic re-programming targets in cancer, in accordance with disclosed embodiments. By leveraging multiple anomaly detectors, genes that maximally reprogram cancer cells towards a wild-type primary expression profile may be identified based on the decision functions (e.g., a distance to a separating manifold, such as a Chebychev distance, a Correlation distance, a Cosine distance, a Euclidean distance, a signed Euclidean distance, a Hamming distance, a Jaccard distance, a Kullback-Leibler distance, a Mahalanobis distance, a Manhattan distance, a Minkowski distance, or a Spearman distance) of the trained models. Here, apoptotic cells were also included to model potential toxicity complications that could arise in healthy cells from a target of interest ("Toxicity" cluster label).

Example 3—a Computational Pipeline for Quantifying Transitions Between Cell States and Identifying Therapeutic Target Genes FIGS. 3A-3C illustrate a computational framework for identifying potential target genes that mediate transcriptional transitions between differentiated or phenotypically distinct cell states following gene interrogation. The transcriptomes of single cells corresponding to disease and target populations of interest were isolated and sequenced. A representative latent space was generated via supervised dimensionality reduction on the distinct cell populations (e.g., UMAP or VAEs), and target genes of interest were identified via pseudotime ordering and trajectory analysis of single cells from the disease state to the target state of interest (as shown in FIGS. 3A and 4A-4D, Example 4). The gene candidates (~100) were then interrogated via transduction with lentivirus harboring a pooled CRISPR interference (CRISPRi) library targeting the candidates. Genes with the most extensive re-programming towards a target state of interest are carried forward for future biological validation.

FIG. 3A shows an example of quantification of re-programming and identification of novel therapeutic target genes, in accordance with disclosed embodiments. By leveraging CRISPR gene interrogation, intelligent latent space construction, and anomaly detection, target genes are quantified in accordance with their ability to program a diseased cell population towards a desired target phenotypic state. The target state may be derived from a healthy tissue or primary cell line or, alternatively, represent an intermediate state including but not limited to: senescent cells, stem cells, precancerous cells, or progenitor cells relevant to disease progression.

As shown in FIGS. 3B-3C, the extent of transcriptional re-programming towards a target state was quantified using anomaly detection (by, e.g., a density-based technique (k-nearest neighbor, local outlier factor, isolation forest), a subspace-based outlier detection, a correlation-based outlier detection, a tensor-based outlier detection, a support vector machine (SVM), a single-class vector machine, support vector data description, a neural network (e.g., replicator neural network, autoencoder, long short-term memory (LSTM) neural network), a Bayesian network, a hidden Markov model (HMM), a cluster analysis-based outlier detection, deviation from association rules and frequent itemsets, fuzzy logic-based outlier detection, and an ensemble technique (e.g., using feature bagging, score normalization, and different sources of diversity).

FIG. 3B shows an example of anomaly detection as a method for defining a dense manifold boundary that accurately represents the topological space occupied by a distinct cell population, in accordance with disclosed embodiments.

FIG. 3C demonstrates an example of this in the context of pancreatic cancer. Briefly, separate anomaly detection models were trained to generate representative manifolds that describe the following differentiated cell populations: pancreatic ductal cells (positive control for re-programming); pancreatic acinar cells (positive control for re-programming); Kras-mutant pancreatic cancer cells expressing a non-target guide RNA (negative control for re-programming); and Kras-mutant pancreatic cancer cells expressing an essential gene targeted (positive control for a toxic target).

As shown in FIG. 3C, the trained anomaly detection models were then applied to score the single-cell RNA-seq profiles of Kras-mutant pancreatic cancer cells targeted with the CRISPRi library. For each target gene of interest, the decision function of the anomaly detector models was used to quantify the extent of transcriptional transition. In practice, the best targets exhibit larger decision functions and effect sizes relative to the negative controls and smaller decision functions and effect sizes relative to the positive controls for re-programming.

Further, as shown in FIG. 3C, by leveraging multiple anomaly detectors, genes that maximally reprogram cancer cells towards a wild-type primary expression profile may be identified based on the decision functions of the trained models. Here, apoptotic cells were also included to model potential toxicity complications that could arise in healthy cells from a target of interest ("Toxicity" cluster label).

Figure 4A:
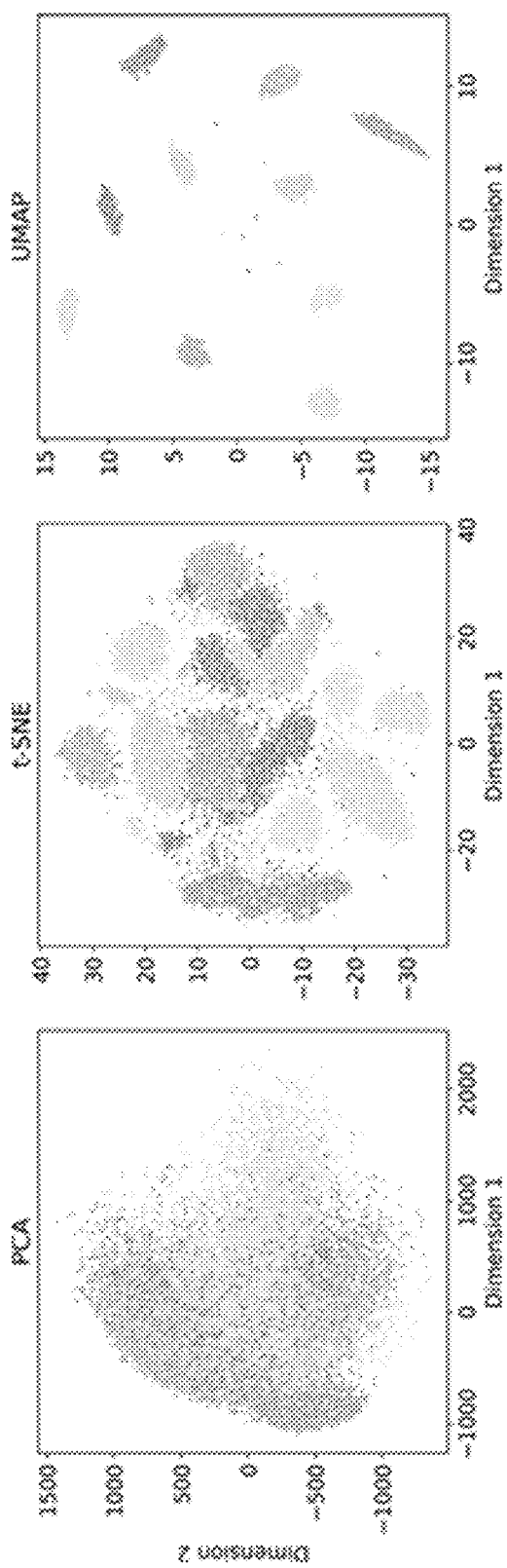
FIG. 4A shows a comparison of several dimensionality reduction algorithms applied to a mixed-cell type dataset, including principal component analysis (PCA), t-distributed stochastic neighbor embedding (t-SNE), and uniform manifold approximation and projection (UMAP), in accordance with disclosed embodiments.

Example 4—UMAP as a Superior Algorithm for Achieving Separability while Preserving Both Fine and Local Structure in Single-Cell RNA-Seq Data FIGS. 4A-4D demonstrate the potential of UMAP for quantifying transitions in single-cell RNA-seq data. FIG. 4A shows a comparison of several dimensionality reduction algorithms applied to a mixed-cell type dataset, including principal component analysis (PCA), t-distributed stochastic neighbor embedding (t-SNE), and uniform manifold approximation and projection (UMAP). As shown in FIG. 4A, supervised dimensionality reduction may be applied to a mixed-cell type dataset, with cell type serving as the supervised label for model training. In contrast with principal component analysis (PCA) and t-distributed stochastic neighbor embedding (t-SNE) embedding, UMAP achieved superior separability while maintaining both fine and global structure in the single-cell data.

Figure 4B:
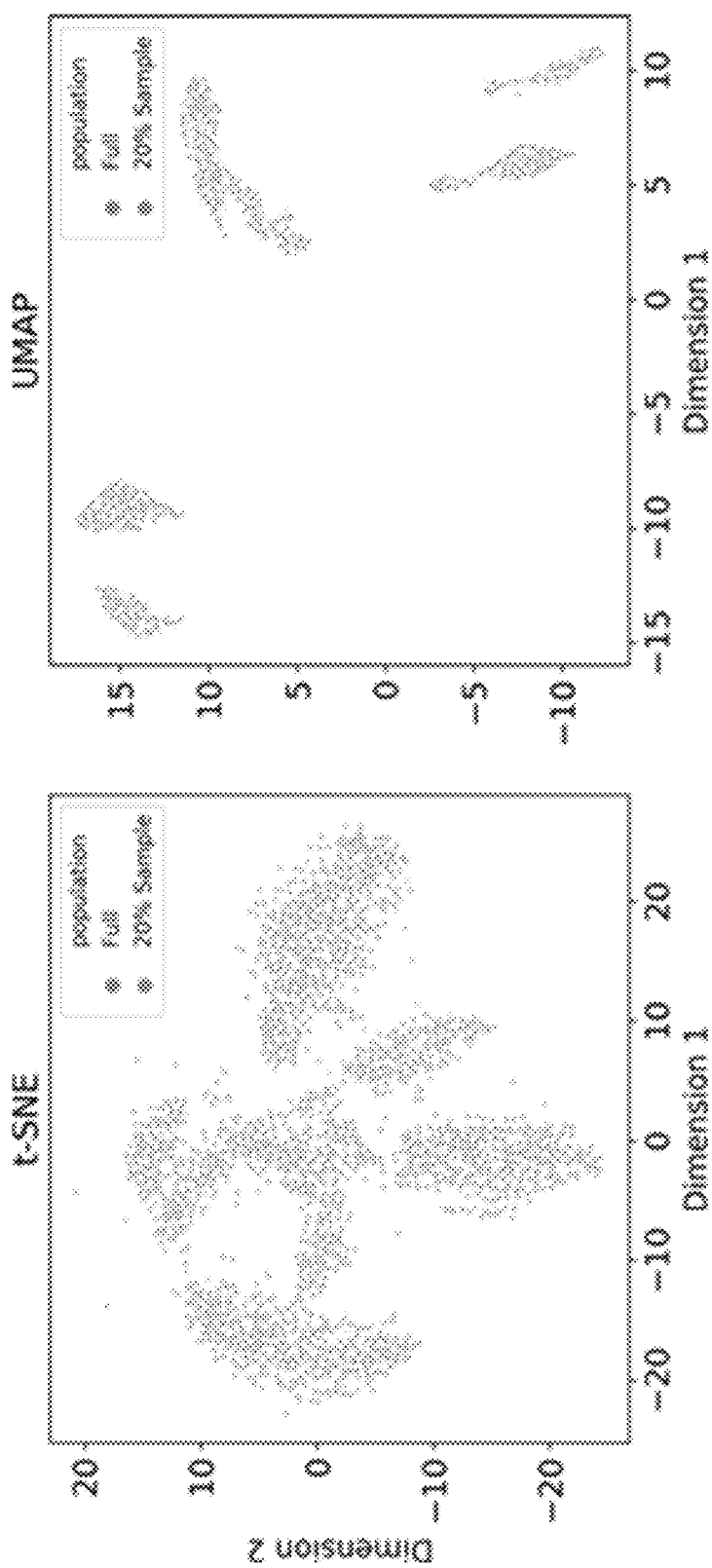
FIG. 4B shows a comparison of latent space stability constructed by t-SNE and UMAP trained on pancreatic ductal, acinar, and adenocarcinoma cell lines, in accordance with disclosed embodiments.

FIG. 4B shows a comparison of latent space stability constructed by t-SNE and UMAP trained on pancreatic ductal, acinar, and adenocarcinoma cell lines. This conceptually illustrates that UMAP achieves greater stability in construction of the supervised latent space. At a fixed random state, the latent space generated from a 20% mixed sample of pancreatic ductal, acinar, and adenocarcinoma cell lines more closely aligns with the full-dataset latent space for the UMAP algorithm.

Figure 4C:
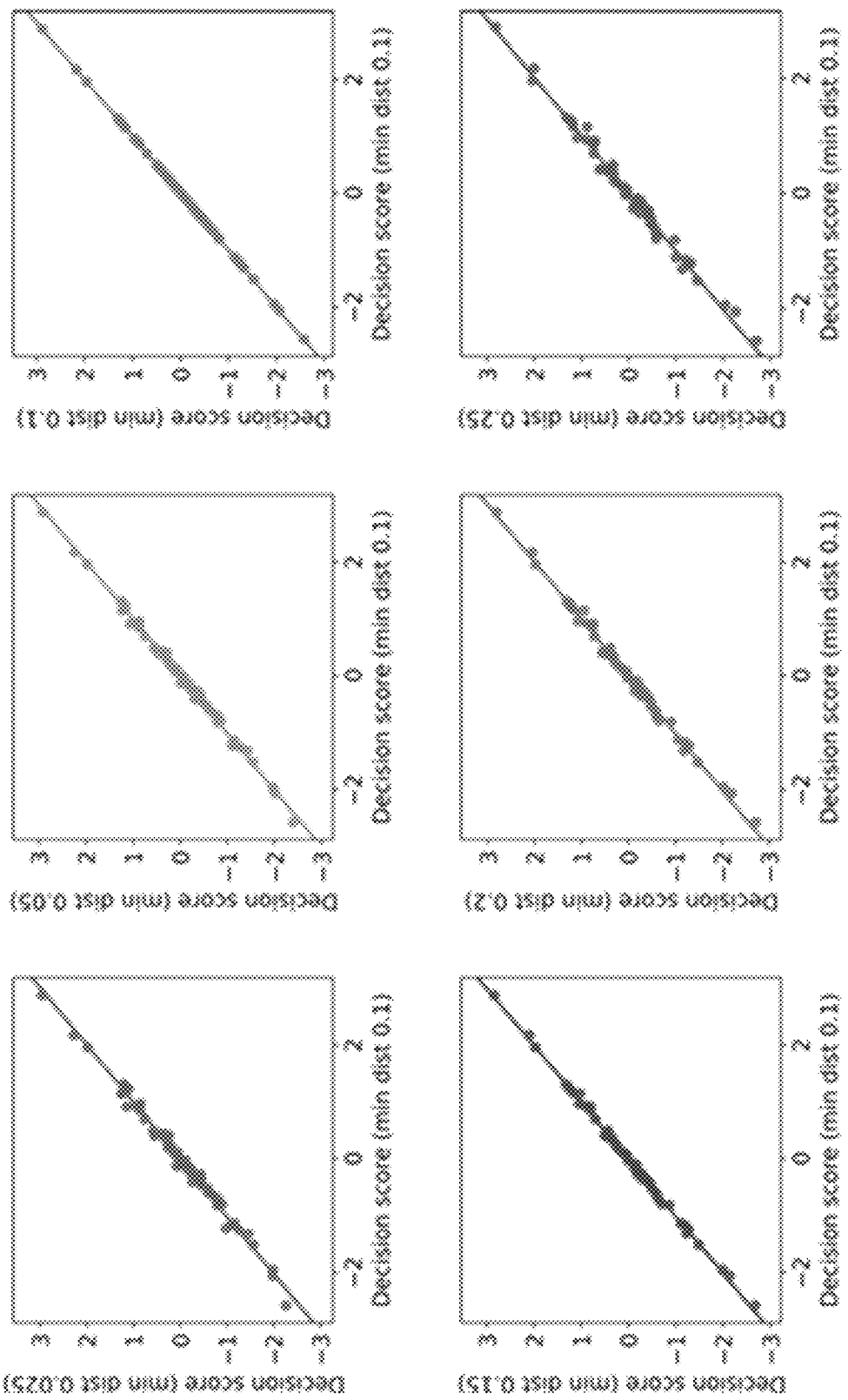
FIG. 4C shows an example of the effect of the UMAP "minimum distance" parameter on quantification of re-programming in pancreatic cancer, in accordance with disclosed embodiments.
Figure 4D:
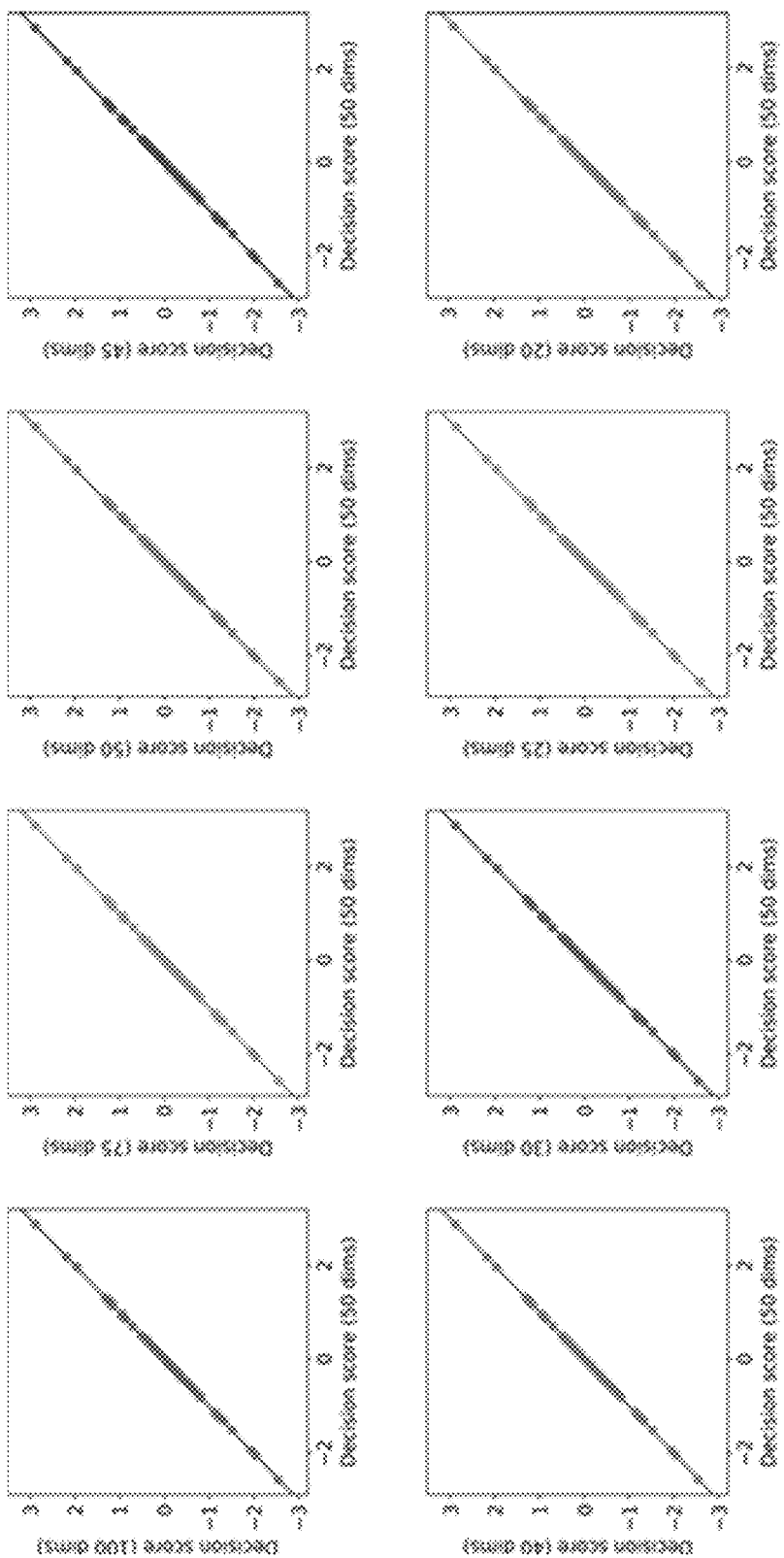
FIG. 4D shows an example of the effect of UMAP latent space dimensionality on quantification of re-programming in pancreatic cancer, in accordance with disclosed embodiments.

FIG. 4C shows an example of the effect of the UMAP "minimum distance" parameter on quantification of re-programming in pancreatic cancer, and FIG. 4D shows an example of the effect of UMAP latent space dimensionality on quantification of re-programming in pancreatic cancer. FIGS. 4C-4D demonstrate the effects of UMAP hyperparameters on quantification of cellular re-programming in pancreatic cancer. The strong correlation in decision scores across a range of conditions demonstrates that quantification of re-programming is robust across a range of reasonable UMAP hyperparameters.

Figure 5A:
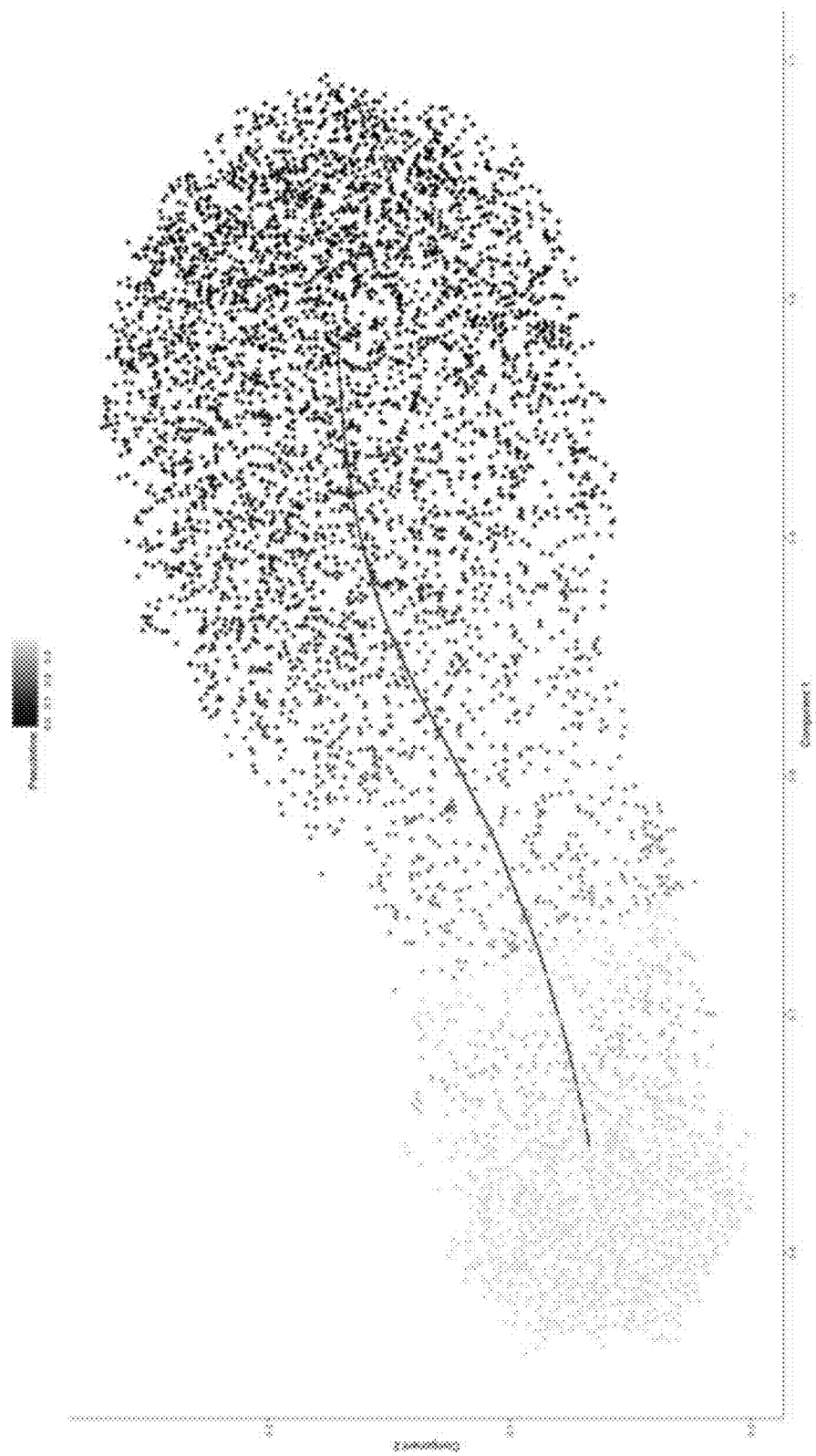
FIG. 5A shows an example of a 2-dimensional projection of pseudo-time ordering produced by the candidate selection pipeline characterizing the transition of pancreatic acinar cells (dark shading on the right) to ductal cells (medium shading in the middle), and subsequently high-grade cancer cells ($Kras^{G12D}$;$p53^{-/-}$;Myc) (light shading on the left), in accordance with disclosed embodiments.

Example 5—Identification of Treatment Target Candidates from Causal Inference Based on Pseudo-Time Principal Tree Constructed from High-Dimensional Single-Cell RNA-Seq Data FIG. 5A demonstrates a 2-dimensional projection of a complete pseudo-time ordering produced by the candidate selection pipeline characterizing the transition of pancreatic acinar cells (dark shading on the right) to ductal cells (medium shading in the middle), and subsequently high-grade cancer cells ($Kras^{G12D}$;$p53^{-/-}$;Myc) (light shading on the left). This is the 2-dimensional projection of the result that maintains the highest separability between these cell populations, for demonstrative purposes. The black curve represents the 2-dimensional projection of the principal trajectory tree learned using the DDRTree Algorithm.

Figure 5B:
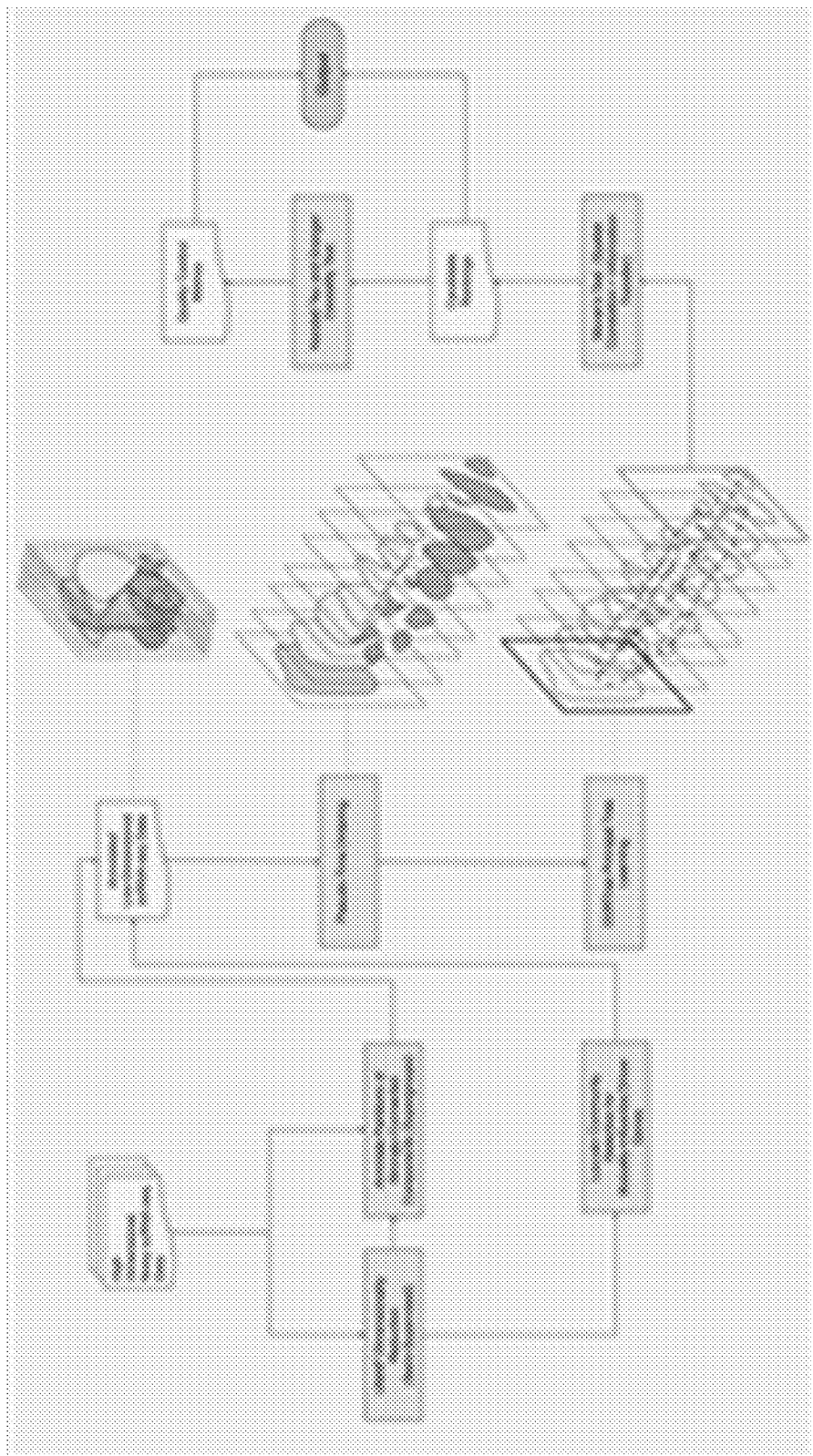
FIG. 5B shows an example of a pipeline for candidate generation from causal inference based on pseudo-time principal tree constructed from high-dimensional single-cell RNA-seq data, in accordance with disclosed embodiments.

FIG. 5B shows an example of a pipeline for candidate generation from causal inference based on pseudo-time principal tree constructed from high-dimensional single-cell RNA-seq data. The initial target candidate selection pipeline orders cells by learning an explicit principal graph from the single-cell data using Reverse Graph Embedding, thereby robustly and accurately resolving the complicated biological processes of pancreatic cancer in these 3 cell types. Each cell may be viewed as a point in a high-dimensional space, where each dimension describes the expression of a different gene in the genome. Identifying the program of gene expression changes is equivalent to learning a trajectory that the cells follow through this space, which may then be used to study the change in expression of important genes through the transition for candidate selection.

In the pre-processing phase of the pipeline, the dimensionality and noise of the scRNA-seq data are reduced using the UMAP Manifold Learning technique, and outliers (usually in the >90% percentiles) were removed based on low expression levels. Next, Monocle3' and the Louvain Algorithm's community detection capabilities were used to label strongly connected components in the resulting low-dimensional representation of the data, which serves as the basis for Pseudo-Time Ordering using Monocle3 and the DDR-Tree Algorithm. This technique orients the samples in a semi-supervised manner using only the labels of the "root" endpoints, which are labeled as the cell populations representing the healthy and diseased states of the transition of interest. DDRTree then learns a spanning graph that connects the endpoints by going through the center of the estimated underlying distributions of points in each cell population through the pseudo-time phases. Genes that drive transition were highlighted using Moran's Test for Spatial Autocorrelation, which incentivizes the selection of "important" causal genes, by assigning a score to genes based on their influence in marking the overall expression of the sample point not only at the endpoints, but also throughout the interpolated transitional phases, as inferred by the learned principal tree. This test produces a ranking of genes that drive the transition of interest, and Kendall Tau and Granger Causality tests were performed to filter outliers and validate strong candidates.

Figure 6A:
FIG. 6A shows an illustration of two anomaly detection algorithms trained on two half-moon scatter plots with random Gaussian noise, in accordance with disclosed embodiments.
Figure 6A:
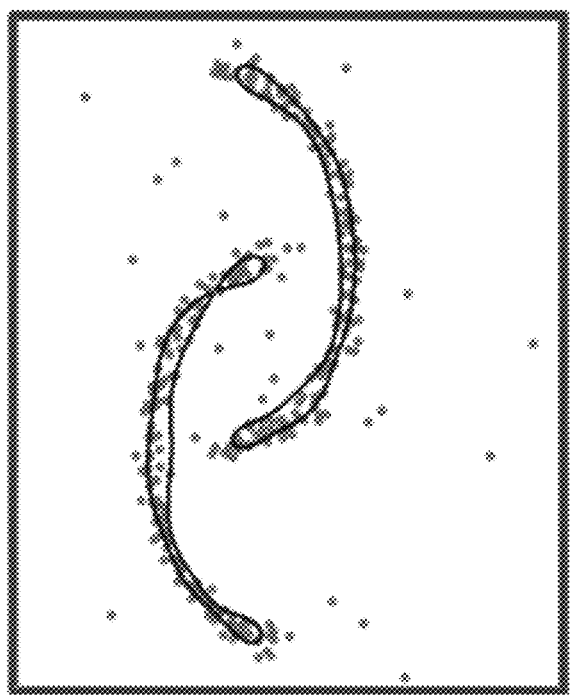
Figure 6B:
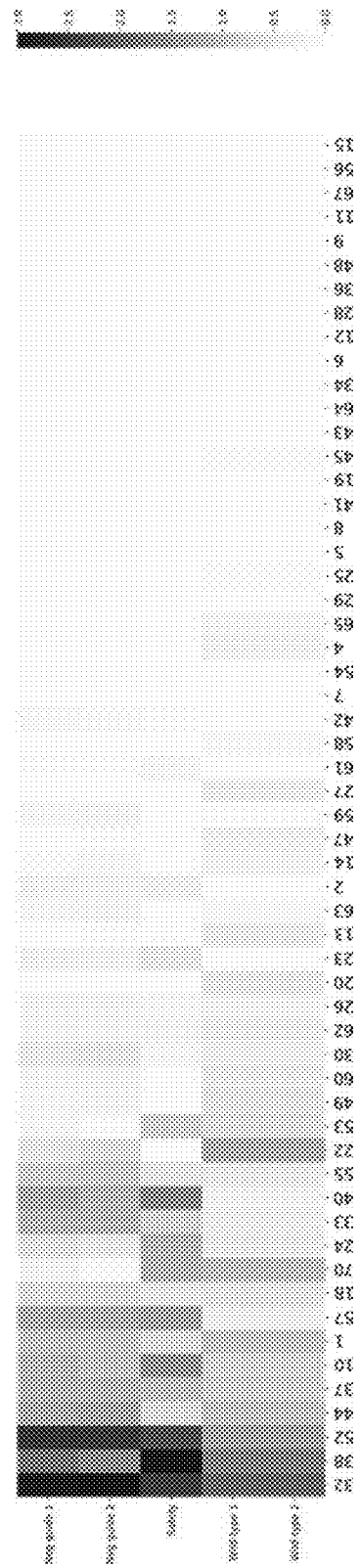
FIG. 6B shows an example of a heatmap of z-transformed anomaly detection decision functions across 70 single guide RNAs (sgRNAs), in accordance with disclosed embodiments. Targets are ordered according to their average ranking across the five trained anomaly detector models. Of the 70 sgRNAs, three resulted in adjusted p-values consistent with significant re-programming towards a primary cell state (32, 52, and 38).
Figure 6C:
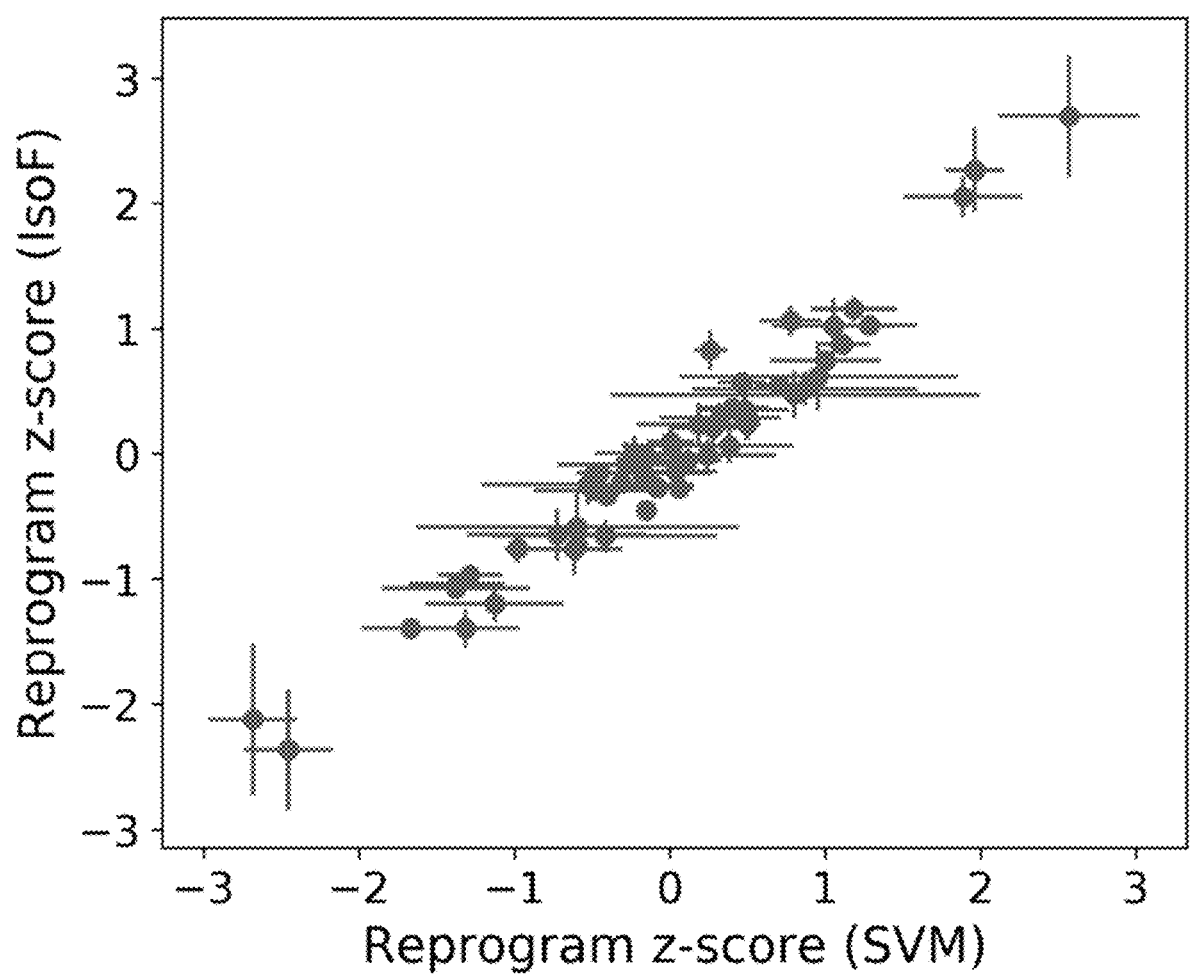
FIG. 6C shows an example of the effects of different anomaly detection algorithms on quantification of re-programming, in accordance with disclosed embodiments. For both algorithms, three targets (32, 52, and 38) resulted in adjusted p-values consistent with significant re-programming. Of the top 10 targets for each algorithm, 8 (80%) were shared.

Example 6—Quantification of Re-Programming in the Latent UMAP Space is Robust Across Different Anomaly Detection Algorithms FIGS. 6A-6C illustrate how the top re-programming target genes may be identified irrespective of choice of anomaly detection algorithm. FIG. 6A shows an illustration of two anomaly detection algorithms trained on two half-moon scatter plots with random Gaussian noise. This provides a visualization of the learned decision manifold boundary for two distinct anomaly detection models (single-class support vector machine and isolation forest) trained on half-moon scatter data with Gaussian noise. FIG. 6B shows a heatmap of z-transformed decision functions for ~70 target sgRNAs across several anomaly detection models relevant to pancreatic cancer. Here, the negative guide columns correspond to negative controls for re-programming, while the wild-type cells correspond to positive controls for re-programming. This heatmap demonstrates how anomaly detectors across multiple cell populations may be used to identify target genes with the greatest potential to reprogram from one differentiated or distinct cell state to another with minimal toxicity. Targets are ordered according to their average ranking across the five trained anomaly detector models. Of the 70 sgRNAs, three resulted in adjusted p-values consistent with significant re-programming towards a primary cell state (32, 52, and 38).

FIG. 6C demonstrates that top re-programming targets may be identified in the UMAP latent space using one of several different anomaly detection algorithms (e.g., a density-based technique (k-nearest neighbor, local outlier factor, isolation forest), a subspace-based outlier detection, a correlation-based outlier detection, a tensor-based outlier detection, a support vector machine (SVM), a single-class vector machine, support vector data description, a neural network (e.g., replicator neural network, autoencoder, long short-term memory (LSTM) neural network), a Bayesian network, a hidden Markov model (HMM), a cluster analysis-based outlier detection, deviation from association rules and frequent itemsets, fuzzy logic-based outlier detection, and an ensemble technique (e.g., using feature bagging, score normalization, and different sources of diversity). For both algorithms, the same three targets (32, 52, and 58) demonstrated significant re-programming away from the negative controls, as measured by the adjusted p-value from a Kolmogorov-Smirnov test. For these three targets, the decision functions additionally met or exceeded the 90th percentile (z-score=1.645) across all of the cell population detectors. Of the top 10 targets, 8 (80%) were shared across both models Example 7—Quantification of Reprogramming and Identification of Target Genes are Robust Across Different Cell Types During Disease Progression Using methods and systems of the present disclosure, anomaly detectors across multiple cell populations were used to identify target genes with the greatest potential to reprogram from high grade to low grade cancer cells. In particular, methods of reprogramming pancreatic triple-mutant cancer cells toward wild-type ductal or acinar cells were developed.

Figure 7A:
FIG. 7A shows an illustration of pancreatic cancer progression and the corresponding cells used for the reprogramming analysis across different stages of cancer development. Pancreatic primary ductal and immortalized acinar cells were used as wild-type cells. Pancreatic cancer cells harboring double mutations ($Kras^{G12D}$;$p53^{-/-}$) were used as low grade cancer cells. Pancreatic cancer cells harboring triple mutations ($Kras^{G12D}$;$p53^{-/-}$;Myc) were used as high grade cancer cells.

FIGS. 7A-7G illustrate how the top target genes can be identified to reprogram high grade cancer cells toward cells at different stages of cancer progression. FIG. 7A shows an illustration of pancreatic cancer progression and the corresponding cells used for the reprogramming analysis across different stages of cancer development. Pancreatic primary ductal and immortalized acinar cells were used as wild-type cells. Pancreatic cancer cells harboring double mutations ($Kras^{G12D}$;$p53^{-/-}$) were used as low grade cancer cells. Pancreatic cancer cells harboring triple mutations ($Kras^{G12D}$;$p53^{-/-}$;Myc) were used as high grade cancer cells.

Figure 7B:
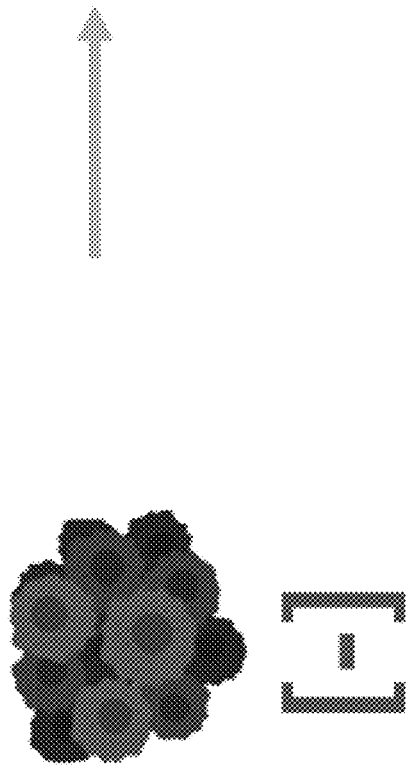
FIGS. 7B-7C show an illustration of the analysis to reprogram pancreatic triple-mutant cancer cells (Kras$^{G12D}$p53$^{-/-}$;Myc) toward wild-type ductal or acinar cells (FIG. 7B), and a heatmap of z-transformed anomaly detection decision functions across 70 single guide RNAs (FIG. 7C), where targets are ordered according to their average ranking across the five trained anomaly detector models.
Figure 7C:
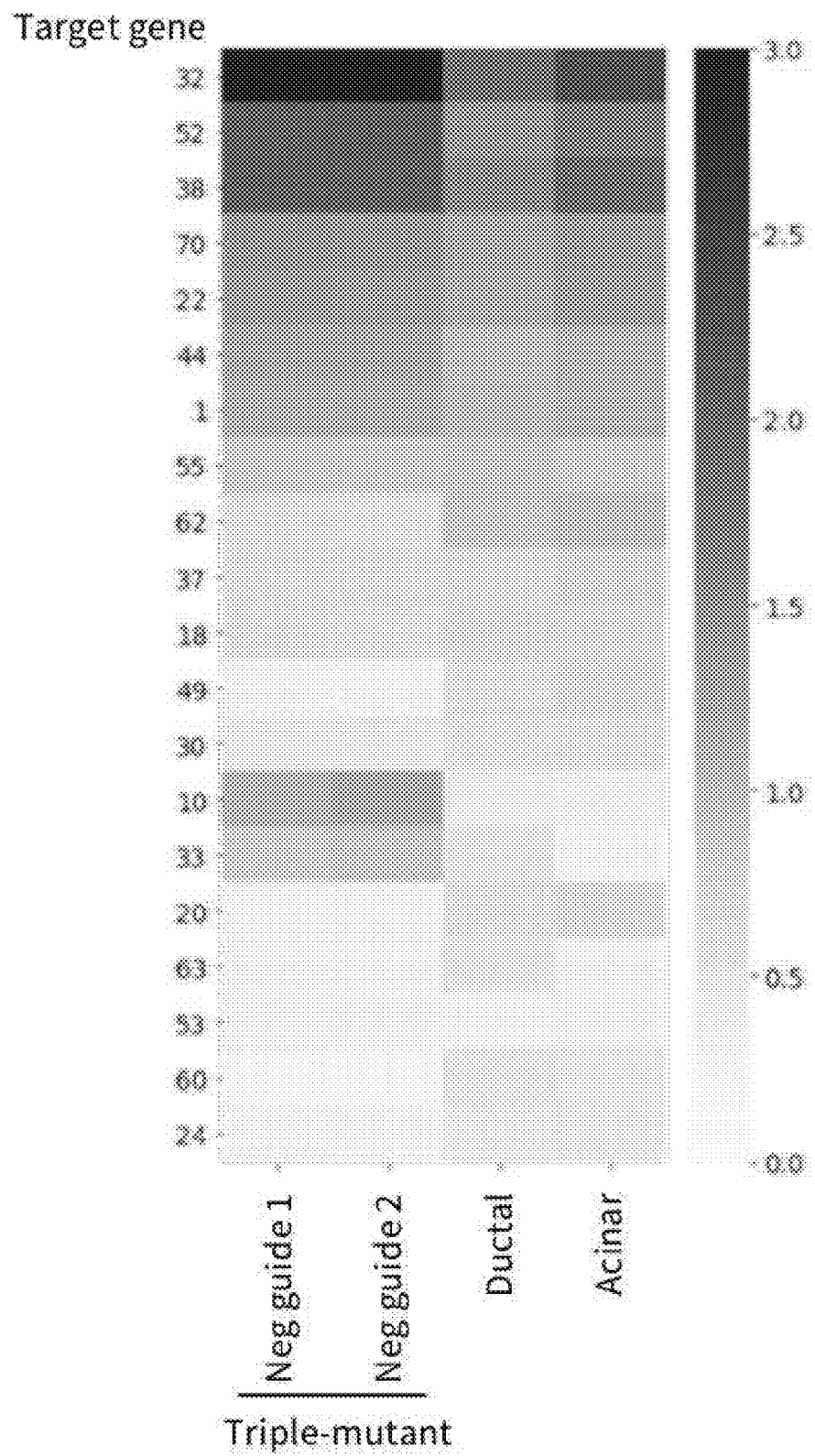

FIGS. 7B-7C show an illustration of the analysis to reprogram pancreatic triple-mutant cancer cells ($Kras^{G12D}$; $p53^{-/-}$;Myc) toward wild-type ductal or acinar cells (FIG. 7B), and a heatmap of z-transformed anomaly detection decision functions across 70 single guide RNAs (FIG. 7C), where targets are ordered according to their average ranking across the five trained anomaly detector models.

FIG. 7C shows a heatmap of z-transformed decision functions for about 70 target sgRNAs across several anomaly detection models relevant to pancreatic cancer. Here, the negative guide columns correspond to negative controls (pancreatic triple-mutant cancer cells harboring negative sgRNAs) for reprogramming, while the wild-type cells (ductal cells and acinar cells) correspond to positive controls for reprogramming. This heatmap demonstrates how anomaly detectors across multiple cell populations can be used to identify target genes with the greatest potential to reprogram from high grade cancer cells to wild-type cells.

Figure 7D:
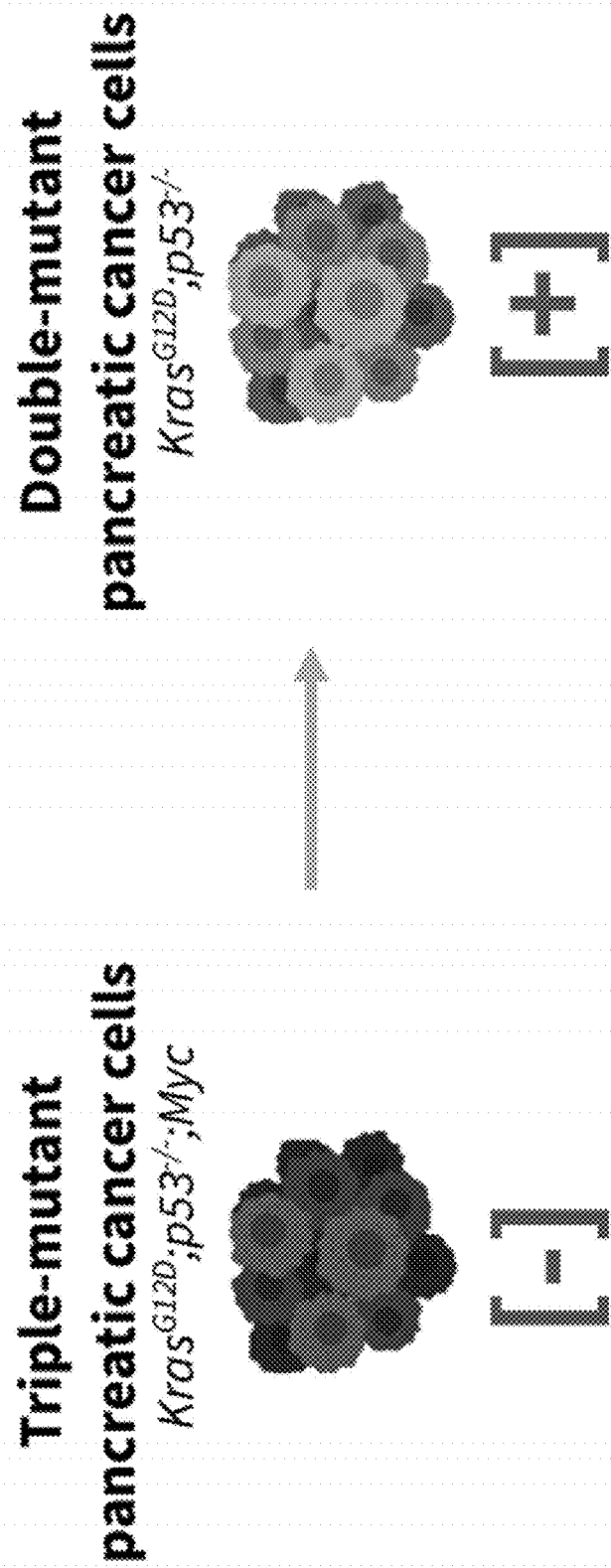
FIGS. 7D-7E show an illustration of the analysis to reprogram pancreatic triple-mutant cancer cells (Kras$^{G12D}$; p53$^{-/-}$;Myc) toward pancreatic double-mutant cancer cells (Kras$^{G12D}$;p53$^{-/-}$) (FIG. 7D), and a heatmap of z-transformed anomaly detection decision functions across 70 single guide RNAs (FIG. 7E), where targets are ordered according to their average ranking across the five trained anomaly detector models.
Figure 7E:
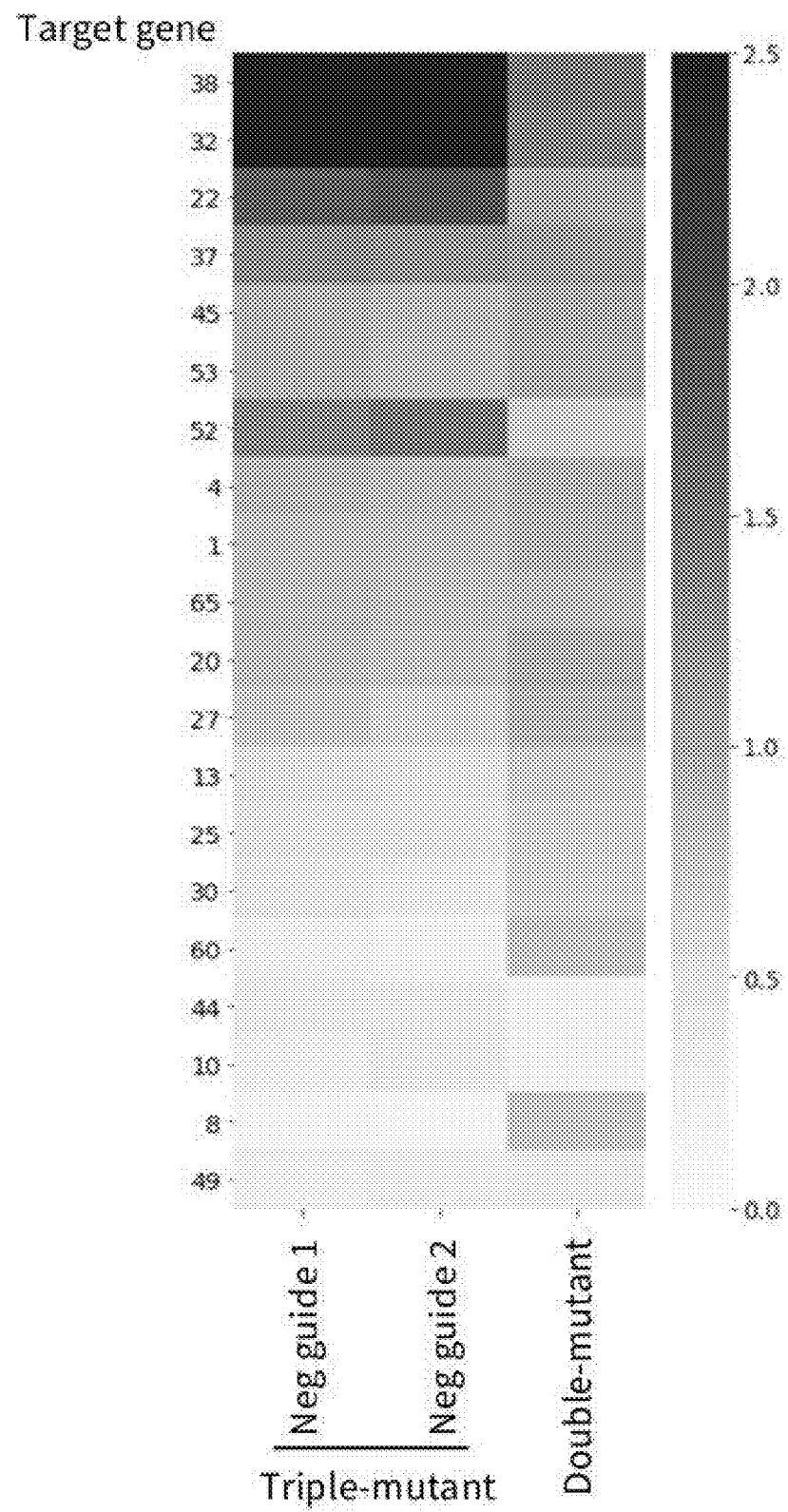

FIGS. 7D-7E show an illustration of the analysis to reprogram pancreatic triple-mutant cancer cells ($Kras^{G12D}$; $p53^{-/-}$;Myc) toward pancreatic double-mutant cancer cells ($Kras^{G12D}$;$p53^{-/-}$) (FIG. 7D), and a heatmap of z-transformed anomaly detection decision functions across 70 single guide RNAs (FIG. 7E), where targets are ordered according to their average ranking across the five trained anomaly detector models.

FIG. 7E shows a heatmap of z-transformed decision functions for about 70 target sgRNAs across several anomaly detection models relevant to pancreatic cancer. Here, the negative guide columns correspond to negative controls (pancreatic triple-mutant cancer cells harboring negative sgRNAs) for reprogramming, while the low grade cancer cells (pancreatic double-mutant cancer cells) correspond to positive controls for reprogramming. This heatmap demonstrates how anomaly detectors across multiple cell populations can be used to identify target genes with the greatest potential to reprogram from high grade to low grade cancer cells.

Figure 7F:
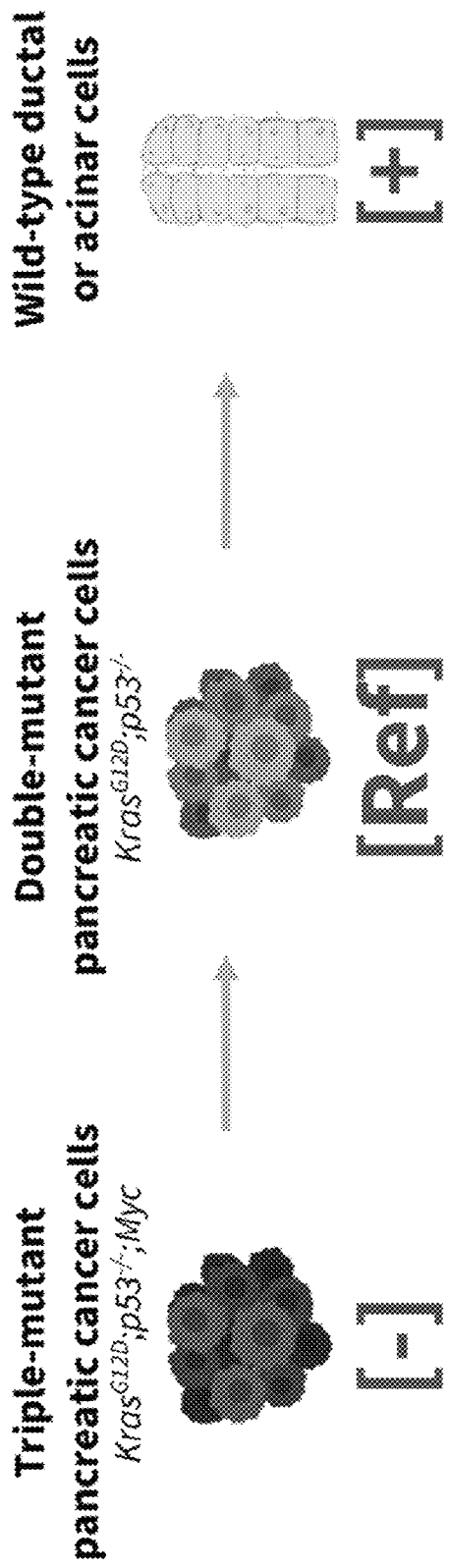
FIGS. 7F-7G show an illustration of the analysis to reprogram pancreatic triple-mutant cancer cells (Kras$^{G12D}$; p53$^{-/-}$;Myc) toward wild-type ductal or acinar cells with pancreatic double-mutant cancer cells (Kras$^{G12D}$;p53$^{-/-}$) as an intermediate cell type (FIG. 7F), and a heatmap of z-transformed anomaly detection decision functions across 70 single guide RNAs (FIG. 7G), where targets are ordered according to their average ranking across the five trained anomaly detector models.
Figure 7G:
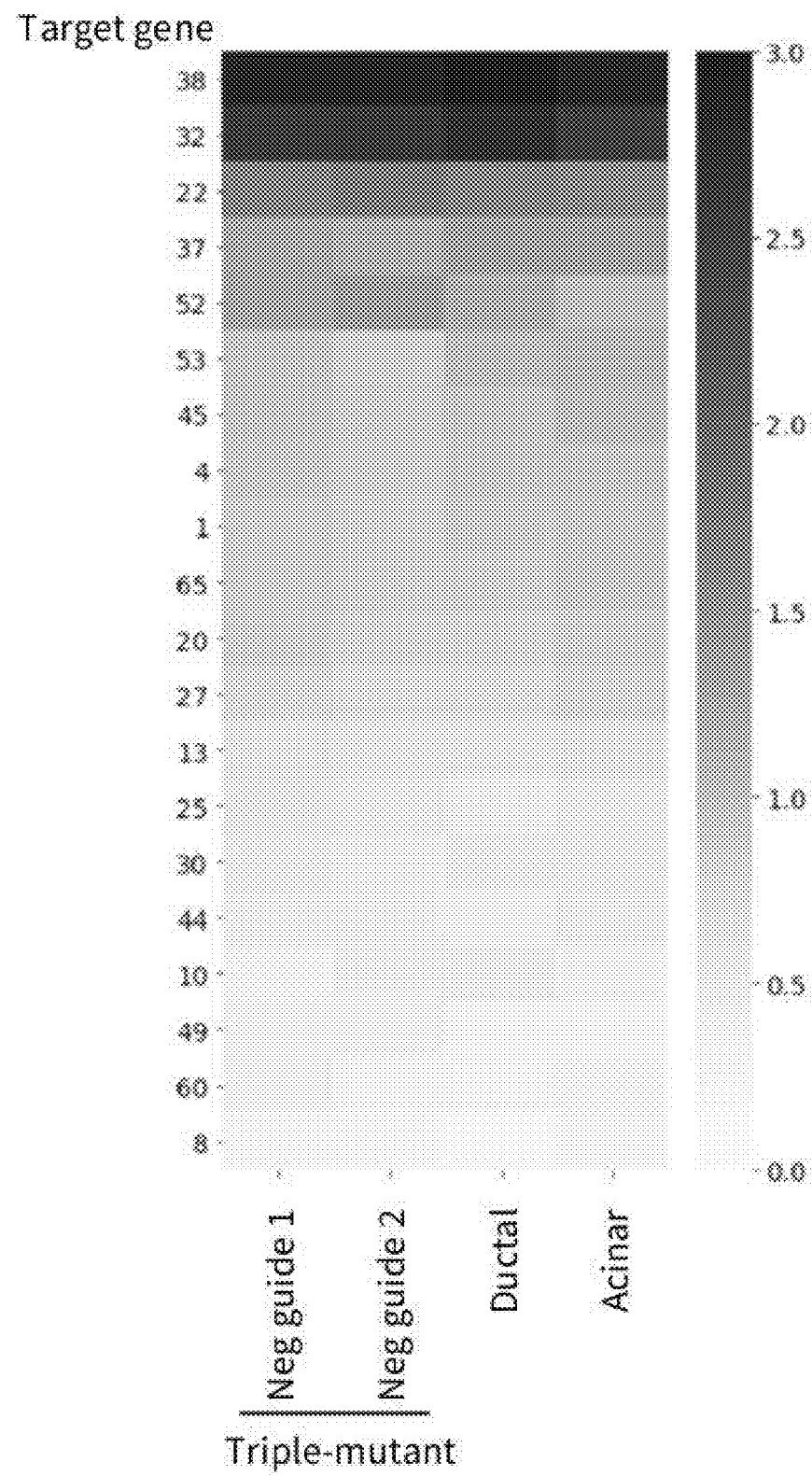

FIGS. 7F-7G show an illustration of the analysis to reprogram pancreatic triple-mutant cancer cells ($Kras^{G12D}$; $p53^{-/-}$;Myc) toward wild-type ductal or acinar cells with pancreatic double-mutant cancer cells ($Kras^{G12D}$;$p53^{-/-}$) as an intermediate cell type (FIG. 7F), and a heatmap of z-transformed anomaly detection decision functions across 70 single guide RNAs (FIG. 7G), where targets are ordered according to their average ranking across the five trained anomaly detector models. In other words, the reprogramming comprised a first reprogramming (pancreatic triple-mutant cancer cells toward pancreatic double-mutant cancer cells) and a second reprogramming (of pancreatic double-mutant cancer cells toward wild-type ductal or acinar cells).

FIG. 7G shows a heatmap of z-transformed decision functions for about 70 target sgRNAs across several anomaly detection models relevant to pancreatic cancer. Here, the negative guide columns correspond to negative controls (pancreatic triple-mutant cancer cells harboring negative sgRNAs) for reprogramming, while the wild-type cells (ductal and acinar cells) correspond to positive controls for reprogramming. In addition, the low grade cancer cells (pancreatic double-mutant cancer cells) were also taken into account in the reprogramming analysis to increase the accuracy and robustness. This heatmap demonstrates how anomaly detectors across multiple cell populations can be used to identify target genes with the greatest potential and strong confidence to reprogram from high grade cancer cells to wild-type cells by taking into account an intermediate cell type in the reprogramming analysis. In particular, cleaner and more robust heatmap data is obtained by adding the intermediate cell type in the reprogramming analysis, which provides better guidance (and thereby improved accuracy) of determining a desired target cell state for reprogramming purposes.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:
1. A method for re-programming a cell, said method comprising:
providing single-cell ribonucleic acid (RNA) sequence data for a plurality of diseased cells and a plurality of normal cells of same cell type as said cell;

mapping at least a portion of said single-cell RNA sequence data into a latent space corresponding to a plurality of phenotypic states of said cell type;

constructing an inferred maximum likelihood progression trajectory from a first phenotypic state to a second phenotypic state of said plurality of phenotypic states, wherein said contracting comprises conducting a non-linear cell trajectory reconstruction on said latent space;

identifying one or more genomic regions that, upon editing, facilitate re-programming of said cell type from said first phenotypic state to said second phenotypic state, wherein said identifying comprises applying probabilistic interference to said inferred maximum likelihood progression trajectory; and editing using a genomic unit, at least one of said identified one or more genomic regions in said cell, thereby re-programming said cell from said first phenotypic state to said second phenotypic state.

2. The method of claim 1, wherein said mapping further comprises applying a dimensionality reduction algorithm to said at least said portion of said single-cell RNA sequence data.

3. The method of claim 2, wherein said dimensionality reduction algorithm comprises a uniform manifold approximation and projection (UMAP) algorithm.

4. The method of claim 3, wherein said UMAP algorithm is a supervised UMAP algorithm.

5. The method of claim 4, wherein said supervised UMAP algorithm has been trained on single-cell RNA sequence data of pure cells of said cell type.

6. The method of claim 4, wherein said supervised UMAP algorithm has been trained using a minimum distance of about 0.025-0.25.

7. The method of claim 1, wherein conducting said non-linear cell trajectory reconstruction on said latent space further comprises applying a reverse graph embedding algorithm to said latent space.

8. The method of claim 1, wherein said first phenotypic state is cancer and said second phenotypic state is a wild-type state.

9. The method of claim 1, further comprising:
prior to said mapping, removing low-frequency genomic regions from said single-cell RNA sequence data for said plurality of diseased cells and said plurality of normal cells.

10. The method of claim 1, wherein said genomic editing unit is selected from the group consisting of a Clustered Regularly Interspaced Short Palindromic Repeats (CRISPR) system, a CRISPR interference (CRISPRi) system, a CRISPR activation (CRISPRa) system, an RNA interference (RNAi) system, and a small hairpin RNA (shRNA) system.

11. The method of claim 1, further comprising:
measuring, using an anomaly detection algorithm, a quantity of a shift in said latent space of said cell responsive to said re-programming of said cell.

12. The method of claim 11, wherein said anomaly detection algorithm has been trained on latent space profiles of a plurality of cell types.

13. The method of claim 12, wherein said plurality of cell types comprises pancreatic ductal cells, pancreatic acinar cells, or pancreatic adenocarcinomas.

14. The method of claim 11, wherein said anomaly detection algorithm comprises one or more of: a density-based technique, a subspace-based outlier detection, a correlation-based outlier detection, a tensor-based outlier detection, a support vector machine (SVM), a single-class vector machine, support vector data description, a neural network, a Bayesian network, a hidden Markov model (HMM), a cluster analysis-based outlier detection, deviation from association rules and frequent itemsets, fuzzy logic-based outlier detection, and an ensemble technique.

15. The method of claim 14, wherein said anomaly detection algorithm comprises said density-based technique, wherein said density-based technique comprises a k-nearest neighbor algorithm, a local outlier factor algorithm, or an isolation forest algorithm.

16. The method of claim 1, further comprising:
measuring a Euclidean distance of a shift in said latent space of said cell responsive to said re-programming of said cell.

17. The method of claim 1, further comprising:
editing, using said genomic editing unit, a respective genomic region of said identified one or more genomic regions in each respective cell of a plurality of cells of said cell type, thereby re-programming each of said plurality of cells between said first phenotypic state and said second phenotypic state;

measuring a quantity of a shift in said latent space of each of said plurality of cells responsive to said re-programming of each of said plurality of cell; and ranking said one or more genomic regions for therapeutic targeting, based at least in part on said measured quantities.

18. The method of claim 1, further comprising:
measuring, using a density estimation function, a quantity of a shift in said latent space of said cell responsive to said re-programming of said cell.

19. The method of claim 1, further comprising generating said single-cell RNA sequence data for said plurality of diseased cells and said plurality of normal cells of said cell type.

20. The method of claim 1, further comprising:
identifying one or more therapeutic targets to treat a disease associated with said first phenotypic state, based at least in part on said identified one or more genomic regions.

21. The method of claim 1, further comprising:
identifying one or more first genomic regions that, upon editing, facilitate re-programming of said cell type between said first phenotypic state and an intermediate phenotypic state of said plurality of phenotypic states; and identifying one or more second genomic regions that, upon editing, facilitate re-programming of said cell type between said intermediate phenotypic state and said second phenotypic state.

22. The method of claim 1, wherein said latent space has a dimensionality between 20 to 100.

* * * * *

UNITED STATES PATENT AND TRADEMARK OFFICE
CERTIFICATE OF CORRECTION

PATENT NO. : 11,710,536 B2
APPLICATION NO. : 17/735494
DATED : July 25, 2023
INVENTOR(S) : Spencer Charles Knight and Chun-Hao Huang It is certified that error appears in the above-identified patent and that said Letters Patent is hereby corrected as shown below:

In the Claims

Claim 1, Line 5:
Replace "normal cells of same cell type as said cell;" with --normal cells of a same cell type as said cell;--.

Claim 1, Line 12: Replace "wherein said contracting comprises conducting a non-" with --wherein said constructing comprises conducting a non- --.

Claim 1, Line 18:
Replace "ing probabilistic interference to said inferred maximum" with --ing probabilistic inference to said inferred maximum--.

Claim 1, Line 20:
Replace "editing using a genomic unit, at least one of said identified" with --editing, using a genomic editing unit, at least one of said identified--.

Claim 17, Line 10:
Replace "ming of each of said plurality of cell" with --ming of each of said plurality of cells--.

Signed and Sealed this
Twenty-second Day of August, 2023

Katherine Kelly Vidal
*Director of the United States Patent and Trademark Office*